(12) United States Patent
Kallmes et al.

(10) Patent No.: US 11,642,143 B2
(45) Date of Patent: May 9, 2023

(54) BALLOON GUIDING SHEATH HAVING AN INFLATION TROUGH

(71) Applicants: Covidien LP, Mansfield, MA (US); Mayo Foundation for Medical Education and Research, Rochester, MN (US)

(72) Inventors: David F. Kallmes, Rochester, MN (US); Waleed Brinjikji, Rochester, MN (US); Brady Hatcher, Rogers, MN (US); Randy Beyreis, Rogers, MN (US)

(73) Assignees: COVIDIEN LP, Mansfield, MA (US); MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 122 days.

(21) Appl. No.: 17/222,392

(22) Filed: Apr. 5, 2021

(65) Prior Publication Data
US 2021/0315594 A1    Oct. 14, 2021

Related U.S. Application Data

(60) Provisional application No. 63/027,009, filed on May 19, 2020, provisional application No. 63/006,794, filed on Apr. 8, 2020.

(51) Int. Cl.
*A61B 17/22* (2006.01)
*A61M 25/10* (2013.01)
(52) U.S. Cl.
CPC .... *A61B 17/22* (2013.01); *A61B 2017/22065* (2013.01); *A61B 2017/22079* (2013.01); *A61M 25/1018* (2013.01)

(58) Field of Classification Search
CPC .............. A61B 17/22; A61B 17/22032; A61B 17/3421; A61B 17/3423;
(Continued)

(56) References Cited

U.S. PATENT DOCUMENTS

| 3,833,003 | A | * | 9/1974 | Taricco | ................. | A61M 25/06 |
| | | | | | | 604/509 |
| 5,728,065 | A | | 3/1998 | Follmer et al. | | |

(Continued)

FOREIGN PATENT DOCUMENTS

| CN | 108969872 A | 12/2018 |
| CN | 109999322 A | 7/2019 |

(Continued)

OTHER PUBLICATIONS

Extended Search Report from counterpart European Application No. 21167140.9, dated Oct. 15, 2021, 9 pp.

(Continued)

*Primary Examiner* — Ashley L Fishback
*Assistant Examiner* — Christian D Knauss
(74) *Attorney, Agent, or Firm* — Shumaker & Sieffert, P.A.

(57) ABSTRACT

A balloon guiding sheath may include an elongated sheath comprising a proximal end, a distal end, an inner tube, an outer tube surrounding the inner tube, an access port, a distal port, and a working lumen extending through an interior portion of the elongated sheath between the access port and the distal port. The balloon guiding sheath may also include an inflatable balloon located on an outer surface of the elongated sheath adjacent the distal end. The balloon guiding sheath may include a plurality of inflation holes extending through a side wall of the elongated sheath. The elongated sheath may be sized and configured to enable direct insertion into a patient's vasculature through an arteriotomy (Continued)

in at least one of a femoral artery and vertebral artery to position the inflatable balloon at a target site.

20 Claims, 18 Drawing Sheets

(58) Field of Classification Search
CPC .......... A61B 2017/22065; A61B 2017/22067; A61B 2017/3486; A61F 2/958; A61M 25/0026; A61M 25/007; A61M 25/10; A61M 25/1018; A61M 25/10181; A61M 2025/0004
See application file for complete search history.

(56) References Cited

U.S. PATENT DOCUMENTS

| | | | |
|---|---|---|---|
| 5,759,191 A | 6/1998 | Barbere | |
| 6,638,245 B2 | 10/2003 | Miller et al. | |
| 6,663,589 B1 * | 12/2003 | Halevy | A61M 25/1027 604/106 |
| 6,702,782 B2 | 3/2004 | Miller et al. | |
| 7,537,580 B2 | 5/2009 | Willard | |
| 9,655,755 B2 | 5/2017 | Chou et al. | |
| 2006/0129175 A1 | 6/2006 | Griffin et al. | |
| 2014/0107575 A1 | 4/2014 | Miller et al. | |
| 2019/0381288 A1 * | 12/2019 | Mock | A61M 25/10 |

FOREIGN PATENT DOCUMENTS

| | | |
|---|---|---|
| GB | 2478988 A | 9/2011 |
| WO | 9830269 | 7/1998 |
| WO | 2017015163 A1 | 1/2017 |
| WO | 2019241520 A1 | 12/2019 |
| WO | 2020018653 A1 | 1/2020 |

OTHER PUBLICATIONS

Response to Communication Pursuant to Rule 70(2) and 70a(2) EPC dated Nov. 22, 2021, from counterpart European Application No. 21167140.9, filed May 16, 2022, 12 pp.

First Office Action and Search Report, and translation thereof, from counterpart Chinese Application No. 202110377827.4 dated Oct. 31, 2022, 21 pp.

\* cited by examiner

BALLOON GUIDING SHEATH HAVING AN INFLATION TROUGH

This application claims the benefit of U.S. Provisional Application No. 63/006,794, filed Apr. 8, 2020, and entitled, "BALLOON GUIDING SHEATH WITH INFLATION TROUGH SYSTEMS AND METHODS" and U.S. Provisional Application No. 63/027,009, filed May 19, 2020, and entitled, "BALLOON GUIDING SHEATH HAVING AN INFLATION TROUGH," each of which is incorporated herein by reference in its entirety.

GOVERNMENT SPONSORED RESEARCH OR DEVELOPMENT

This invention was made with government support under NS103670 awarded by the National Institutes of Health. The Government has certain rights in the invention.

TECHNICAL FIELD

The disclosure relates generally to medical devices and methods of use. Embodiments of the invention include devices for performing thrombectomy or embolectomy in the internal carotid artery and other vessels of a patient.

BACKGROUND

Mechanical thrombectomy is a procedure that removes clots through endovascular intervention to restore blood flow to the brain during acute ischemic stroke. Acute Ischemic Stroke ("AIS") can be caused by thrombus, embolus or other occlusions in regions of the internal carotid artery ("ICA") such as the Petrous segment, Cavernous segment or Cerebral segment, or the middle cerebral artery ("MCA"), such as the MCA bifurcation, the M1 segment, and the M2 segment. Approaches for performing thrombectomy or embolectomy to treat AIS include accessing the vasculature and navigating a balloon guiding catheter to the carotid artery at a location upstream from the occlusion, typically at a proximal location in the artery such as the cervical segment of the ICA. After the balloon is inflated to provide antegrade blood flow cessation, retrieval devices can be passed through the balloon guide catheter to retrieve the embolus. Thrombectomy tools such as stent retrievers, aspiration catheters, or both can be delivered directly to the embolus through the guiding catheter to complete the retrieval process, after which the balloon is deflated and the retrieval and guide catheters retracted to the access point. These thrombectomy procedures may involve placing a sheath through an arteriotomy in the patient's common femoral artery, and delivering the guiding catheter to the ICA through the sheath. In some cases, the arteriotomy may be located in an artery other than the common femoral artery. For example, an 8-9 French (Fr) inner diameter (ID) (0.015-0.118 inches) sheath having a length on the order of twenty-five centimeters can be used to provide the access to the arterial tree through the arteriotomy. A balloon guiding catheter having a 7-8 Fr outer diameter (OD) (0.092-0.105 inches), commonly about ninety centimeters in length, can then be delivered to the ICA through the sheath. An arteriotomy of 0.131-0.144 inches may be required for the sheath during procedures of these types. Unfortunately, these relatively large arteriotomies can enhance the risk of bleeding, especially since patients undergoing these procedures may be receiving thrombolytics that may increase the risks of hemorrhagic complications.

Distal access aspiration catheters (e.g., up to about 0.087 inch OD) are sometimes used during thrombectomy in the ICA. Such distal aspiration catheters include the ACE 68 from Penumbra, Inc. and the Sophia Plus from Microvention, Inc. For example, during these procedures the distal aspiration catheter can be inserted with the end positioned at the distal middle cerebral artery. Other thrombectomy tools such as stent retrievers are sometimes delivered to the intracranial vasculature through distal access catheters used in this manner, or directly through the guide catheter. However, balloon guiding catheters have IDs that are too small to accommodate these distal aspiration catheters. Other known balloon guide catheters include the Cello devices from Medtronic, Inc., and the Flowgate2 device from Stryker Neurovascular. The relatively long period of time required to place a sheath and then a balloon guide catheter can detract from the benefits of this treatment.

Stent retrievers and other endovascular tools are sometimes placed in the ICA or other vasculature using guiding sheaths that do not have balloons. Guiding sheaths are typically about ninety centimeters in length. These devices act as a combination of access sheath and guiding catheter. The need for a separate sheath is obviated by the use of these guiding sheaths since they are sufficiently long to provide access to the target vessel. Although guiding sheaths do not provide arterial occlusion, they can be rapidly placed.

SUMMARY

The disclosure includes a balloon guiding sheath comprising an elongated sheath comprising a proximal end, a distal end, an inner tube extending between the proximal end and the distal end, an outer tube surrounding the inner tube and extending between the proximal end and the distal end, an access port located adjacent the proximal end, a distal port located adjacent the distal end, and a working lumen extending through an interior portion of the elongated sheath between the access port and the distal port; an inflatable balloon located on an outer surface of the elongated sheath adjacent the distal end, the inflatable balloon being fluidly coupled to an inflation lumen extending between the inflatable balloon and an inflation port located adjacent the proximal end; and a plurality of inflation holes extending through a side wall of the elongated sheath, wherein the plurality of inflation holes fluidly couple the inflatable balloon to the inflation lumen. The elongated sheath may be sized and configured to enable direct insertion into a patient's vasculature through an arteriotomy in at least one of a carotid artery and vertebral artery to position the inflatable balloon at a target site.

In some embodiments, the balloon guiding sheath further comprises an inflation trough located on the outer tube, wherein the inflation trough facilitates fluid coupling between each inflation hole of the plurality of inflation holes. The inflation trough may rotationally extend around at least a portion of a perimeter of the outer tube to fluidly couple two inflation holes of the plurality of inflation holes. In some embodiments, the inflation trough rotationally extends 360-degrees around the perimeter of the outer tube to fluidly couple each inflation hole of the plurality of inflation holes. The elongated sheath may be elongate along a first direction, and the inflation trough may rotationally extend along a second direction that is perpendicular to the first direction.

In some embodiments, the plurality of inflation holes are substantially symmetrically spaced around the outer tube. The plurality of inflation holes and the inflation trough may be arranged and configured to facilitate substantially symmetrical inflation of the inflatable balloon. In some embodiments, the inflation trough is located between the outer tube and the inflatable balloon. The inflation trough may be located adjacent the distal end of the elongated sheath. In some embodiments, the inflation trough is located closer to a distal portion of the inflatable balloon than a proximal portion of the inflatable balloon.

In some embodiments, the elongated sheath is elongate along a first direction, and the inflation trough defines a depth radially extending along a second direction that is perpendicular to the first direction. In some embodiments, the elongated sheath is elongate along a first direction, the plurality of inflation holes each define a first width extending along the first direction, and the inflation trough defines a second width extending along the first direction, and wherein the first width is greater than the second width. The elongated sheath may define a generally constant outer diameter from the proximal end to the distal end.

The disclosure also includes a method of using a balloon guiding sheath comprising an elongated sheath comprising a proximal end, a distal end, an inner tube extending between the proximal end and the distal end, an outer tube surrounding the inner tube and extending between the proximal end and the distal end, an access port located adjacent the proximal end, a distal port located adjacent the distal end, a working lumen extending through an interior portion of the elongated sheath between the access port and the distal port, an inflatable balloon located on an outer surface of the elongated sheath adjacent the distal end, the inflatable balloon being fluidly coupled to an inflation lumen extending between the inflatable balloon and an inflation port located adjacent the proximal end, a plurality of inflation holes extending through a side wall of the elongated sheath that fluidly couple the inflatable balloon to the inflation lumen, and an inflation trough located on the outer tube, the inflation trough configured to facilitate fluid coupling between each inflation hole of the plurality of inflation holes. In some embodiments, the method comprises inserting the balloon guiding sheath directly into a patient's vasculature through an arteriotomy in at least one of a carotid artery or a vertebral artery; advancing the balloon guiding sheath through the patient's vasculature and positioning the distal end at a target site; and inflating the inflatable balloon with at least one of fluid and media via the plurality of inflation holes and the inflation trough.

In some embodiments, the method further comprises substantially symmetrically inflating the inflatable balloon via the plurality of inflation holes and the inflation trough. The method may include applying a substantially even inflation force into the inflatable balloon, via the plurality of inflation holes and the inflation trough, whereby the inflation force radially extends around a perimeter of the elongated sheath and the inflation force is directed away from the elongated sheath to thereby substantially symmetrically inflate the inflatable balloon. In some embodiments, the method includes maintaining a substantially constant and even pressure within the inflatable balloon.

In some embodiments, wherein prior to the inflating the distal end of the elongated sheath is located in a first position with respect to the target site, the method further comprises, while inflating, maintaining a location of the distal end of the elongated sheath such that the distal end is substantially located in the first position during the inflating. The method may include, after inflating, maintaining the location of the distal end of the elongated sheath such that the distal end is still substantially located in the first position after the inflating.

In some embodiments, the inflating comprises injecting, via the inflation port, at least one of fluid and media into the inflation lumen through the plurality of inflation holes and the inflation trough and into the inflatable balloon.

The elongated sheath may be elongate along a first direction, and the inflation trough may define a depth radially extending along a second direction that is perpendicular to the first direction, and the method may further comprise sending the at least one of fluid and media through the inflation lumen along the first direction; sending the at least one of fluid and media through the plurality of inflation holes along the second direction; sending the at least one of fluid and media through the inflation trough rotationally around the outer tube; and sending the at least one of fluid and media radially along the second direction away from the elongated sheath to thereby inflate the inflatable balloon.

BRIEF DESCRIPTION OF THE DRAWINGS

These and other features, aspects, and advantages are described below with reference to the drawings, which are intended to illustrate, but not to limit, the invention. In the drawings, like reference characters denote corresponding features consistently throughout similar embodiments.

DETAILED DESCRIPTION

Figure 1:
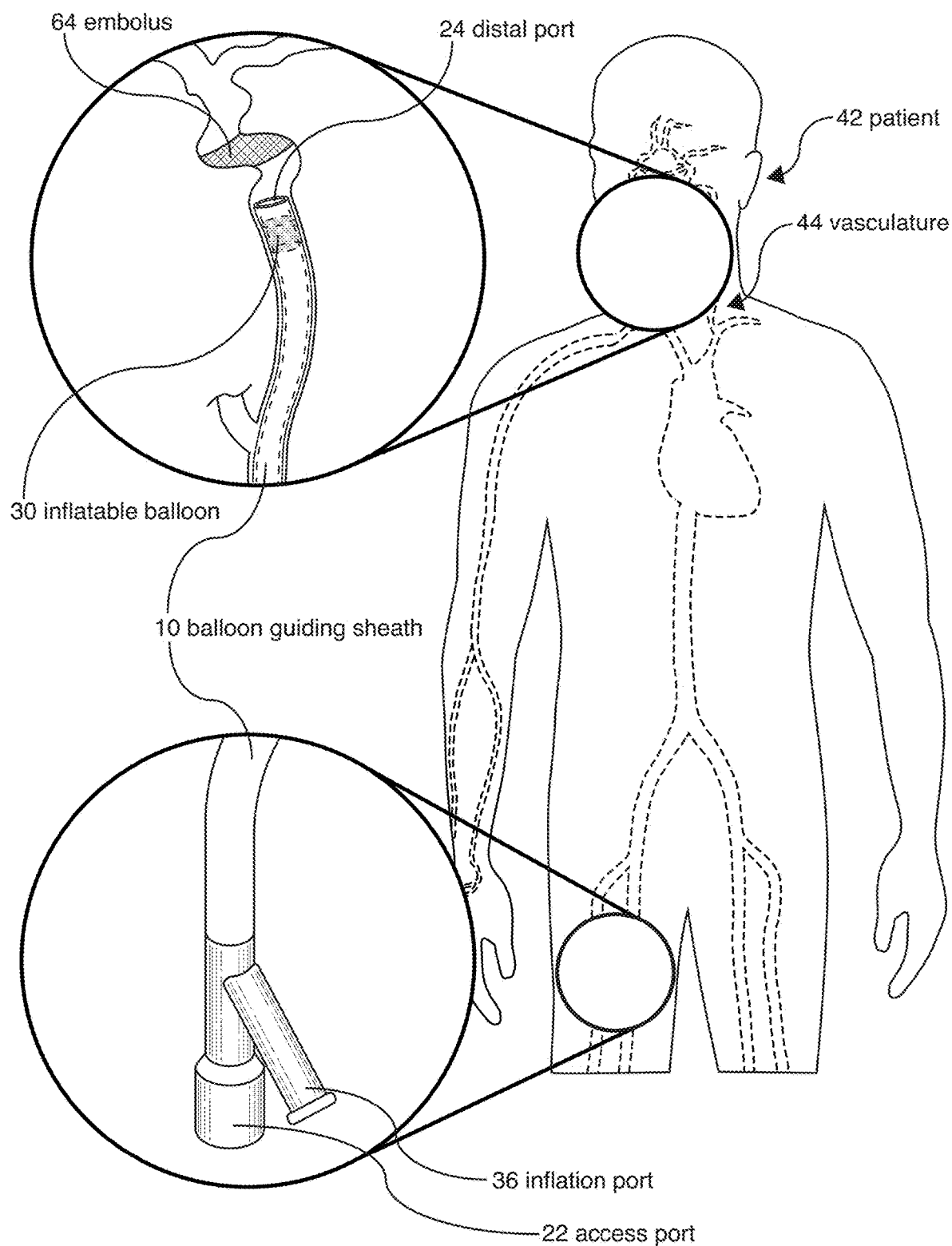
FIG. 1 illustrates a diagrammatic view of a balloon guiding sheath in a patient, according to some embodiments.

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

COMPONENT INDEX

- 10—balloon guiding sheath
- 12—elongated sheath
- 14—proximal end (of elongated sheath)
- 16—distal end (of elongated sheath)
- 18—inner tube
- 20—outer tube
- 22—access port
- 24—distal port
- 26—working lumen
- 28—interior portion
- 30—inflatable balloon
- 34—inflation lumen
- 36—inflation port
- 38—at least one inflation hole
- 38a—inflation hole
- 38b—inflation hole
- 38c—inflation hole
- 42—patient
- 44—vasculature
- 44a—common carotid artery
- 44b—internal carotid artery
- 44c—external carotid artery
- 44d—middle cerebral artery
- 44e—anterior cerebral artery
- 46—arteriotomy
- 48—target site
- 50—inflation trough
- 52—perimeter (of outer tube)
- 54—distal portion (of inflatable balloon)
- 56—proximal portion (of inflatable balloon)
- 60—first width
- 62—second width
- 64—embolus There is a continuing need for improved devices and methods for performing mechanical revascularization such as thrombectomy and embolectomy in the ICA and other vasculature. In particular, there is a need for such devices and methods that provide effective navigation to the target artery, support while advancing retrieval devices, and rapid flow arrest. Devices and methods of these types that can improve the efficiency of health care delivery would be especially desirable.

FIG. 1 illustrates a diagrammatic view of a patient 42 undergoing a thrombectomy procedure using a balloon guiding sheath 10, which, in many embodiments, is a balloon guide catheter capable of direct arterial access without an introducer sheath. As shown in FIG. 1, in some embodiments, the balloon guiding sheath 10 is sized and configured to be inserted in an arteriotomy located on the thigh of the patient 42 in order to reach a target site via femoral access. The arteriotomy may be located in another area of the patient's 42 vasculature 44, such as near the groin of the patient 42 in order to reach the target site via the patient's 42 femoral artery. In some embodiments, the arteriotomy is located near the wrist of the patient 42 to reach the target site via transradial arterial access. The arteriotomy may also be located in the patient's 42 vertebral artery. In many embodiments, the target site is located in a carotid artery of the patient 42.

As shown in FIG. 1 and as will be discussed in greater detail later in the disclosure, in some embodiments the balloon guiding sheath 10 includes an inflatable balloon 30, which, in many embodiments, is located on an outer surface of an elongated sheath 12 (not shown in FIG. 1) and near a distal end of the elongated sheath 12. The balloon guiding sheath 10 may also include an access port 22 and an inflation port 36, both of which may be located near a proximal end of the elongated sheath 12. In some embodiments, the balloon guiding sheath 10 includes a distal port 24 located near a distal end of the elongated sheath 12.

Figure 2:
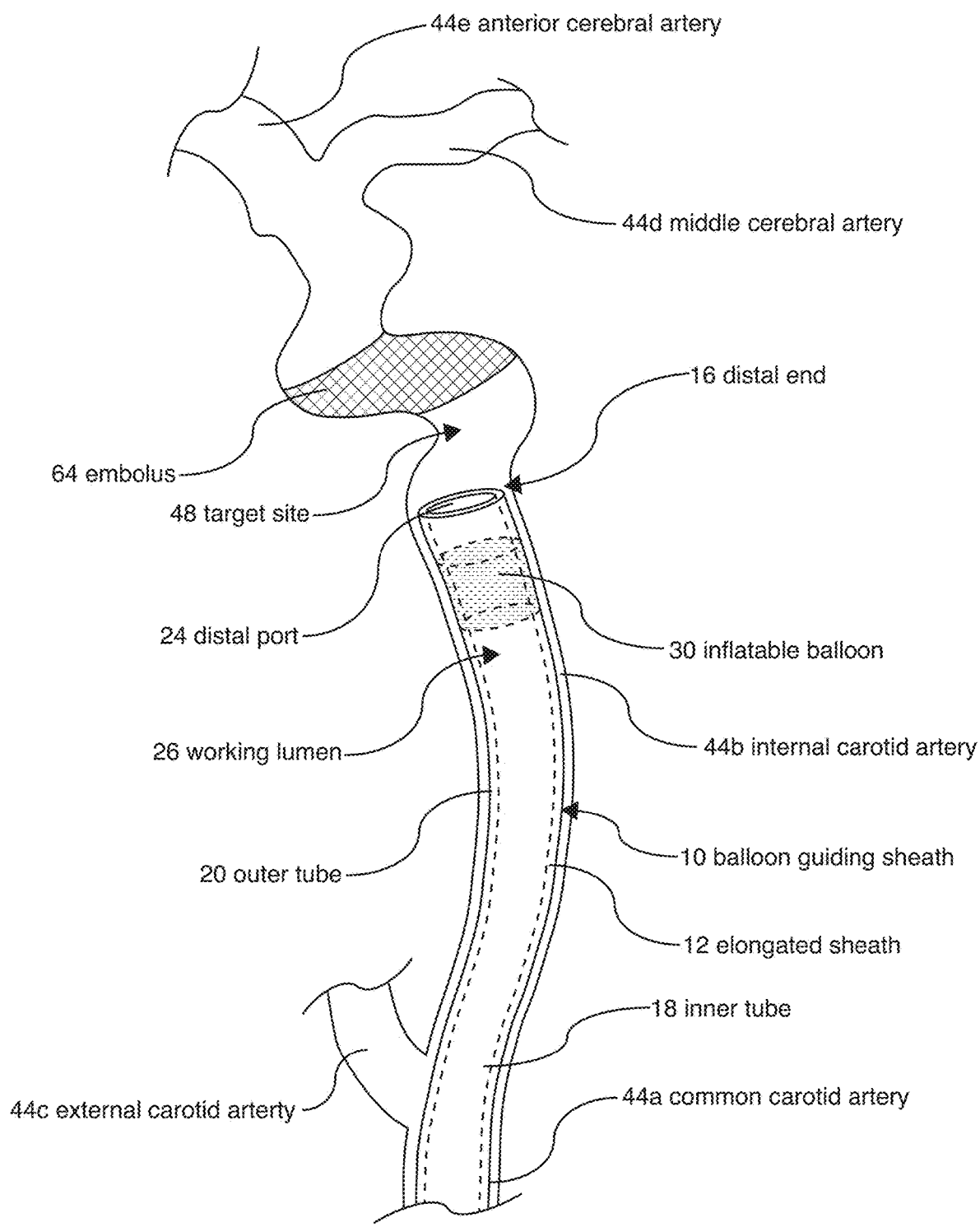
FIGS. 2 and 3 illustrate perspective views of a balloon guiding sheath, according to some embodiments.

FIG. 2 illustrates a perspective view of the balloon guiding sheath 10 located inside the vasculature 44. Specifically, FIG. 2 includes the common carotid artery ("CCA") 44a, which branches into the internal carotid artery ("ICA") 44b and the external carotid artery ("ECA") 44c. As shown, the middle cerebral artery ("MCA") 44d and the anterior cerebral artery ("ACA") 44e are located near a distal portion of the ICA 44b. FIG. 2 shows, in greater detail, the distal end 16 of the elongated sheath 12, including the distal port 24, located adjacent a target site 48. In many embodiments, the target site 48 is located adjacent an occlusion in a vessel, such as an embolus 64, as illustrated by FIG. 2. Occlusions, such as an embolus 64, are commonly located in the ICA 44b and near the MCA 44d, as shown in FIG. 2. As demonstrated by FIG. 1 as well as FIG. 2, the elongated sheath 12 may also include an inflatable balloon 30, which may be located adjacent the distal end 16. In some embodiments, the inflatable balloon 30 extends to a distal edge of the elongated sheath 12. The inflatable balloon 30 may also be located near, but not extend all the way to, the distal end 16, as illustrated in FIG. 2.

In some embodiments, the inflatable balloon 30 is configured to inflate, thereby pausing a substantial amount of the blood flow through the vasculature 44 to the target site 48. Methods of inflating the balloon 30 will be discussed later in the disclosure. Once blood flow has been reduced and/or temporarily stopped, the balloon guiding sheath 10 may be configured to remove the embolus 64 through the distal port 24. Removal of the embolus 64 may be achieved through suction, as in an aspiration thrombectomy procedure, and/or with the use of an additional device that physically breaks up the embolus 64, as in a mechanical thrombectomy procedure. In some embodiments, the additional device is inserted through the access port 22 of the balloon guiding sheath 10, illustrated in FIG. 1.

FIG. 2 also shows that, in some embodiments, the balloon guiding sheath 10 includes an inner tube 18 and an outer tube 20. The outer tube 20 may substantially surround the inner tube 18, and both the inner and outer tubes 18, 20, may extend between the proximal end and the distal end 16 of the elongated sheath 12. The balloon guiding sheath 10 may also include a working lumen 26, which, in some embodiments, extends through an interior portion of the elongated sheath 12 between the distal port 24 and the access port 22. The working lumen 26 may be configured to enable removal of an embolus 64 by providing a passageway for suction and/or an additional device used for mechanical thrombectomy.

Figure 3:
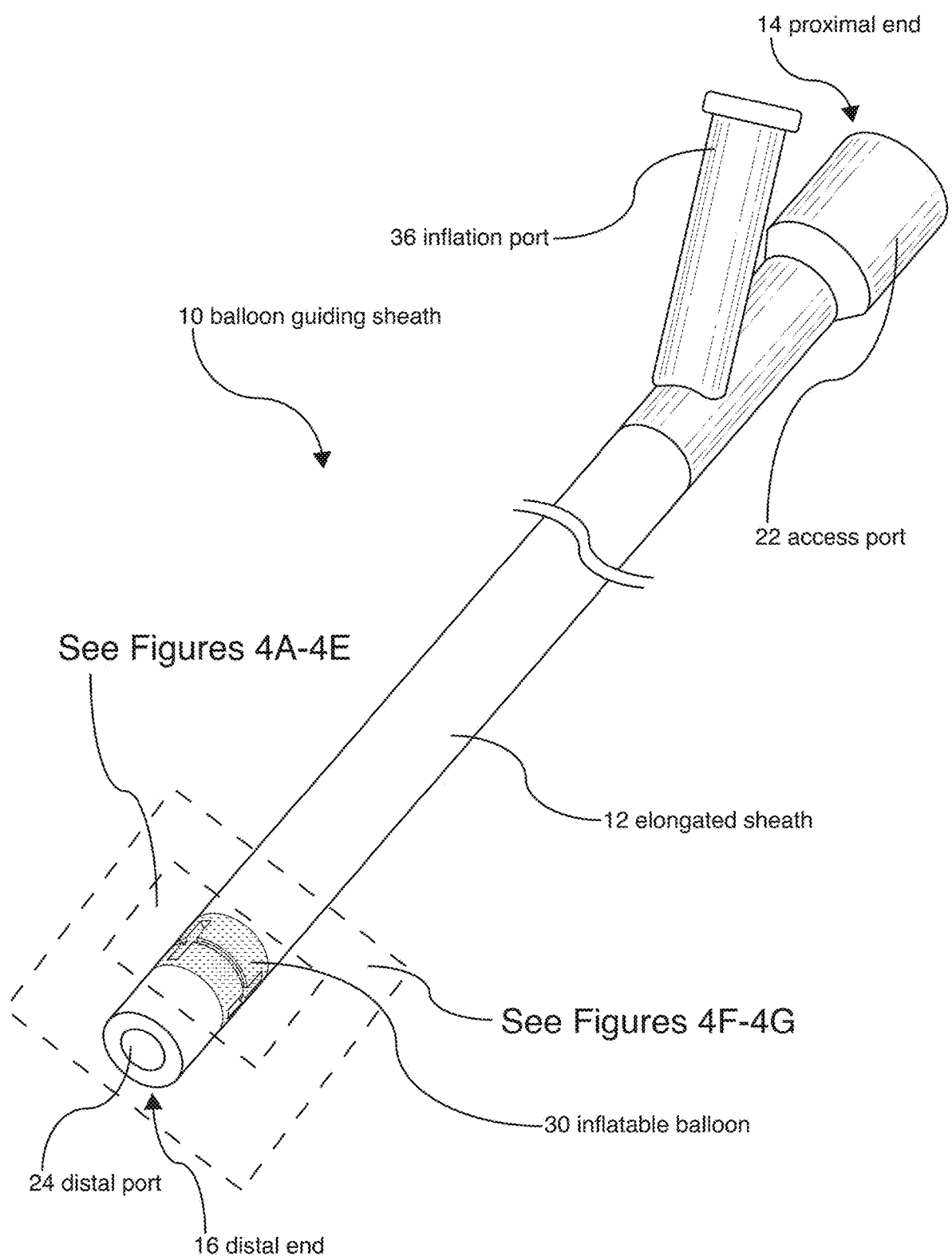

FIG. 3 illustrates another perspective view of the balloon guiding sheath 10, according to some embodiments. As shown, in some embodiments, the inflatable balloon 30 and the distal port 24 are located at and/or adjacent the distal end 16 and the access port 22 and inflation port 36 are located at and/or adjacent the proximal end 14. The inflation port 36 may be configured to enable inflation of the inflatable balloon 30. In some embodiments, inflation of the inflatable balloon 30 is achieved by the injection of at least one of fluid and media through the inflation port 36. The inflatable balloon 30 may be located on an outer surface of the elongated sheath 12, and may wrap around substantially an entire circumference of the elongated sheath 12. As shown in FIG. 3, in some embodiments, the inflatable balloon 30 is located on top of additional components of the elongated sheath 12. These additional components will be discussed in more detail with reference to FIGS. 4A-4G, as indicated in FIG. 3.

In many embodiments, the elongated sheath defines a generally constant outer diameter from the proximal end 14 to the distal end 16. The balloon guiding sheath 10 may define a length of about ninety centimeters.

Figure 4A:
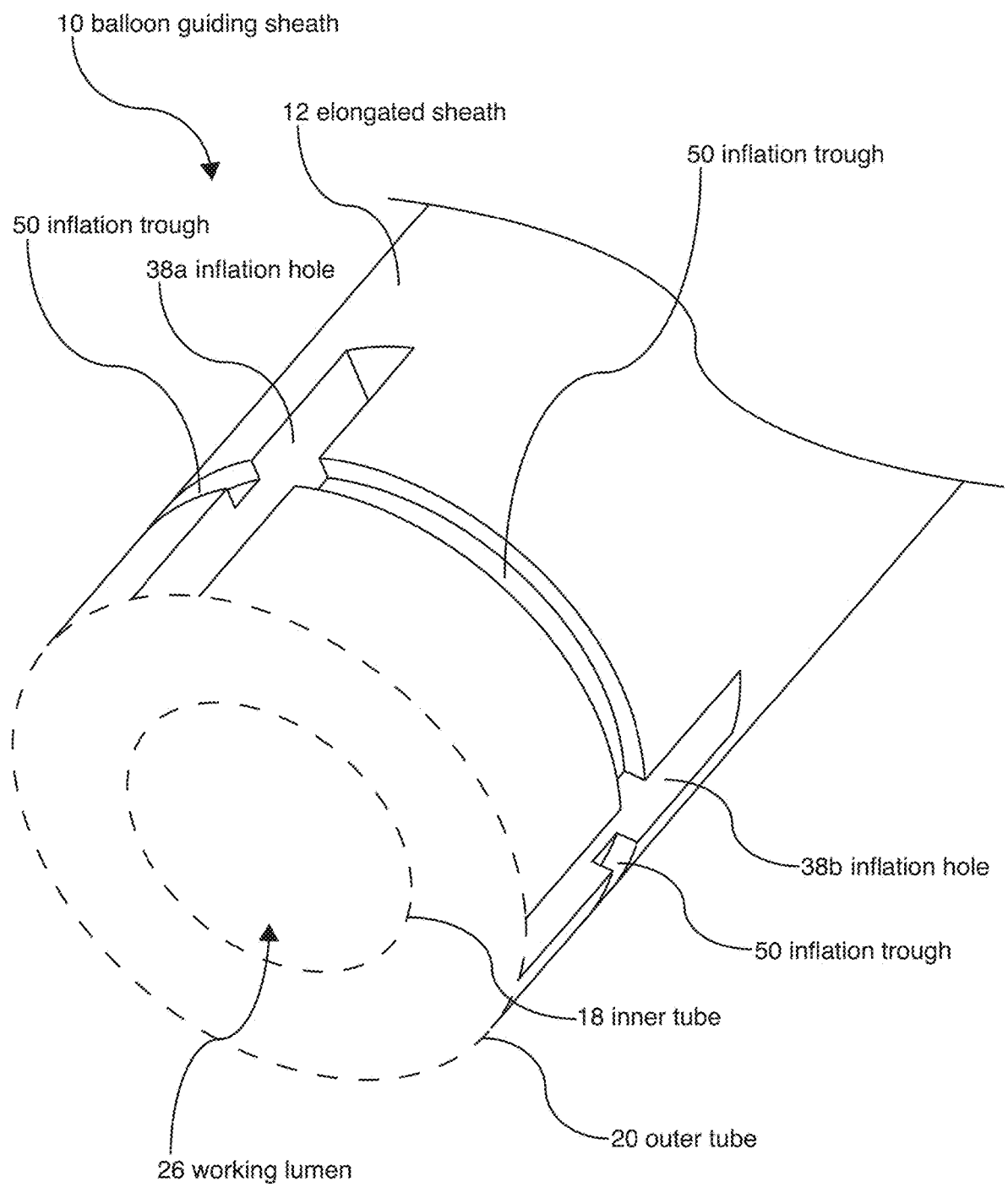
FIGS. 4A, 4B, 4C, 4D, 4E, 4F, and 4G illustrate perspective views of a portion of a balloon guiding sheath including at least one inflation hole and an inflation trough, according to some embodiments.

FIGS. 4A-4E show perspective views of a portion of the elongated sheath 12, including at least one inflation hole 38 and an inflation trough 50. It should be noted that, for ease of illustrating the at least one inflation hole 38 and the inflation trough 50, FIGS. 4A-4E do not include the inflatable balloon 30 and the distal most portion of the elongated sheath 12. As will be described in greater detail, in many embodiments the elongated sheath 12 comprises at least one inflation hole 38 configured to enable substantially symmetrical inflation of the inflatable balloon 30. It should be noted that "symmetrical inflation" is intended to indicate radial symmetry of the inflated balloon 30. As such, when inflated in a "substantially symmetrical" manner, the inflatable balloon 30 comprises a substantially consistent diameter from a proximal portion to a distal portion of the balloon 30. As illustrated in FIG. 4A, in some embodiments, the elongated sheath 12 comprises three inflation holes 38a, 38b, and 38c. The inflation trough 50 may also be configured to work with the at least one inflation hole 38 to achieve inflation of the inflatable balloon 30, in some embodiments, the inflation trough 50 aids in achieving substantial symmetrical inflation of the inflatable balloon 30.

FIG. 4A also shows, in greater detail, the inner tube 18 and outer tube 20 previously mentioned with reference to FIG. 2. It should be noted that the outer tube 20 and inner tube 18 are illustrated with dashed lines to represent that the portion of the elongated sheath 12 included in FIG. 4A does not necessarily extend to the distal end 16. FIG. 4A also includes the working lumen 26, which, in some embodiments, extends through an interior portion of the elongated sheath 12 between the distal port 24 and the access port 22.

Figure 4B:
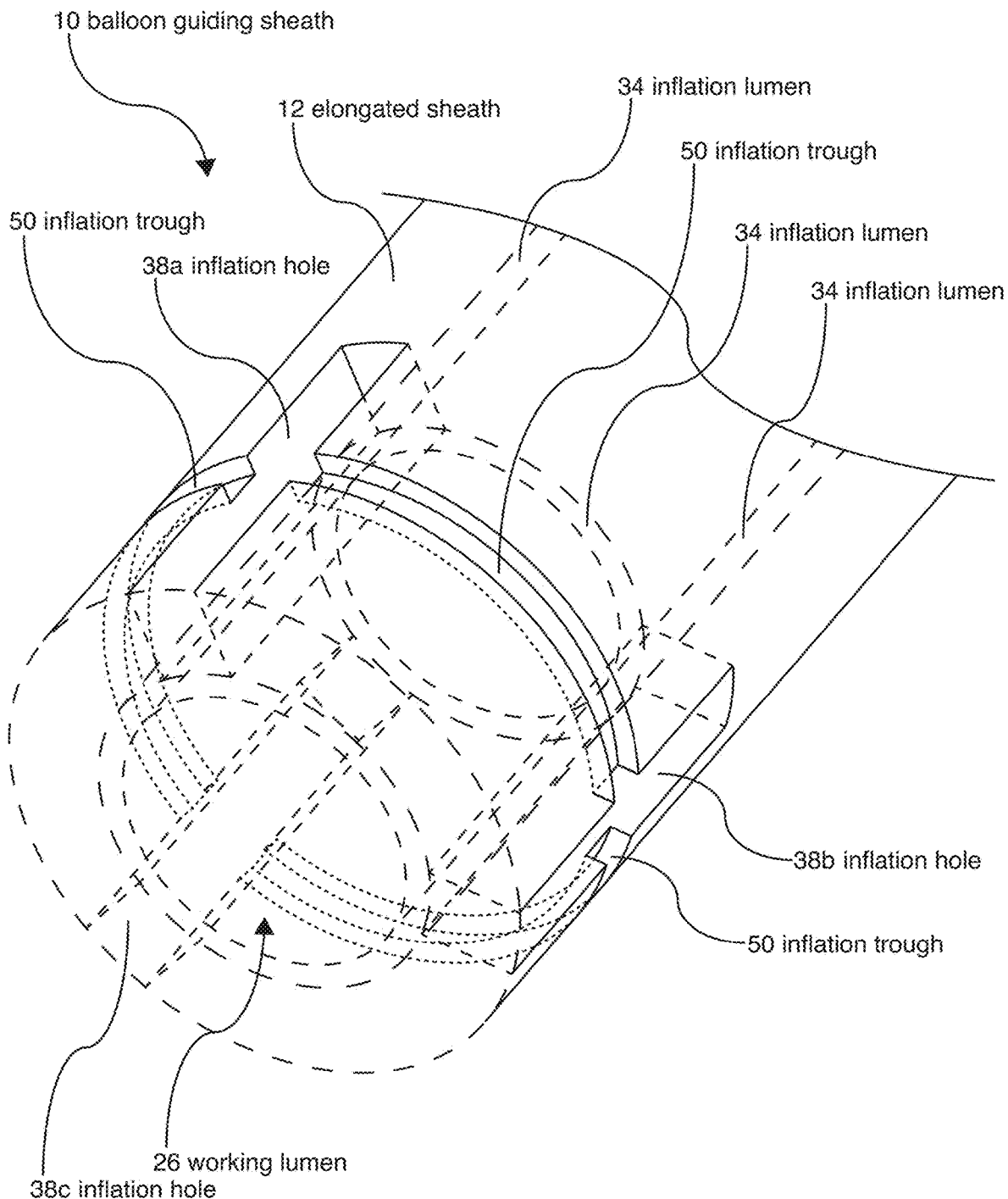

FIG. 4B illustrates a similar view as that of FIG. 4A, but also includes interior elements (shown in dashed lines) of the balloon guiding sheath 10, including the working lumen 26, the inflation lumen 34, the at least one inflation hole 38, and the inflation trough 50. In many embodiments, the balloon guiding sheath 10 comprises an inflation lumen 34 that extends between the inner tube 18 and the outer tube 20. The inflation lumen 34 may be configured to carry the at least one of fluid and media from the inflation port 36, shown in FIG. 3, to the inflatable balloon 30, thereby enabling inflation of the inflatable balloon 30. The fluid coupling between the inflation lumen 34 and the inflatable balloon 30 may also enable deflation of the balloon 30 by withdrawing the at least one of fluid and media from the balloon 30, through the inflation lumen 34, and out through the inflation port 36.

Figure 4C:
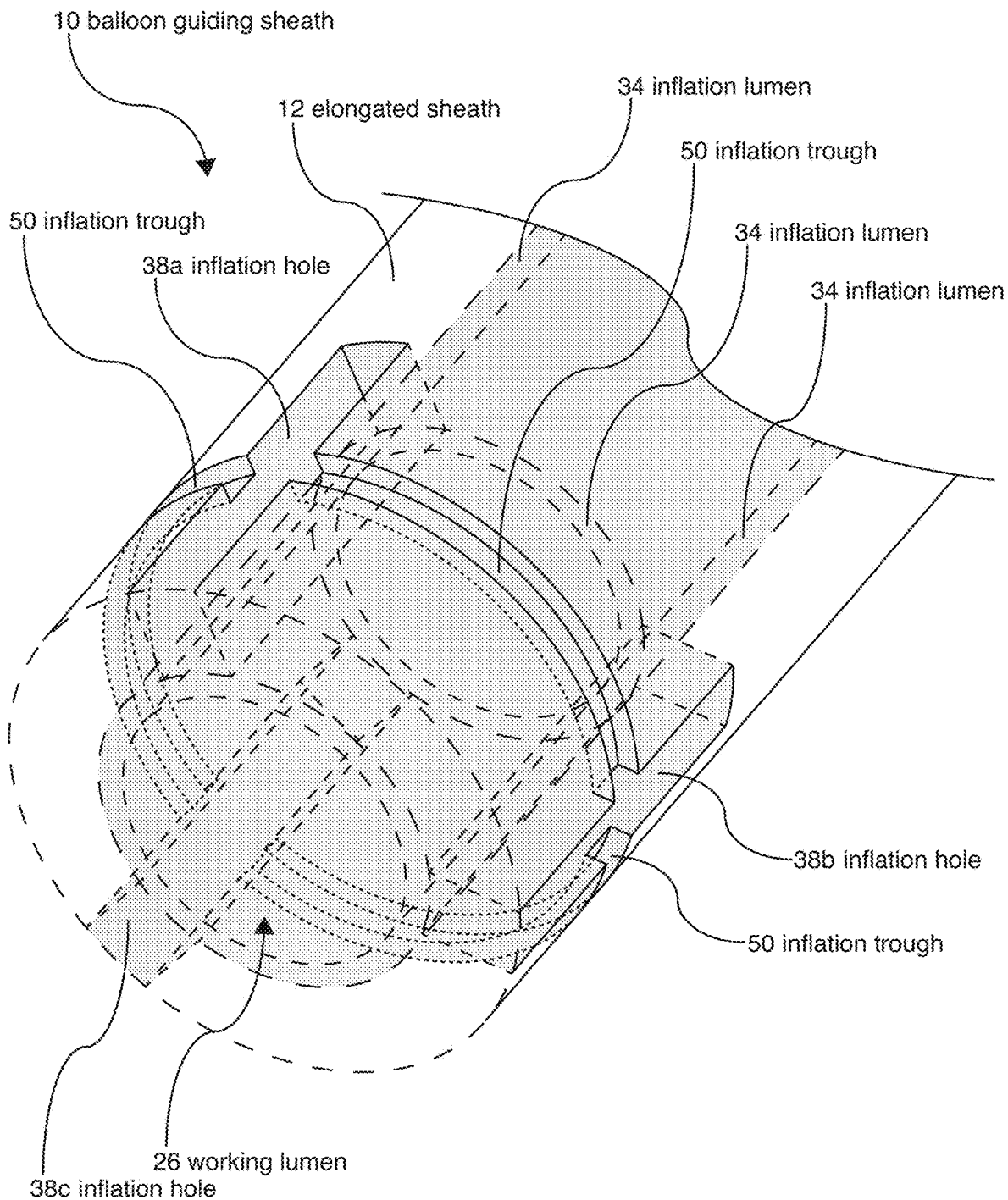

In many embodiments, the inflation lumen 34 is fluidly coupled to the inflatable balloon 30 via at least one of the at least one inflation hole 38 and the inflation trough 50. FIG. 4C illustrates the fluidly coupled areas, which are distinguished from the other components with shading. It should be noted that, in some embodiments, the inflation lumen 34 surrounds the working lumen 26. As such, FIG. 4C may appear to show shading of the working lumen 26. However, this shaded area actually represents the inflation lumen 34 and in many embodiments, the working lumen 26 is not fluidly coupled to the inflation trough 50 and the at least one inflation hole 38.

The elongated sheath 12 may comprise at least one inflation hole 38 located adjacent a distal portion of the elongated sheath 12. In some embodiments, and as illustrated by FIG. 4A-4G, the elongated sheath 12 comprises three inflation holes 38a, 38b, and 38c substantially evenly spaced around, and extending through, a side wall of the elongated sheath 12. The side wall may be the outer tube 20, such that the outer tube 20 defines the at least one inflation holes 38. In some embodiments, the elongated sheath 12 comprises at least one inflation hole 38 substantially symmetrically spaced around the outer tube 20 of the elongated sheath 12. The elongated sheath 12 may comprise a number other than three inflation holes (e.g. such as two holes, four holes, five holes, nine holes, twenty-five holes), which may be substantially evenly spaced from one another.

Figure 4D:
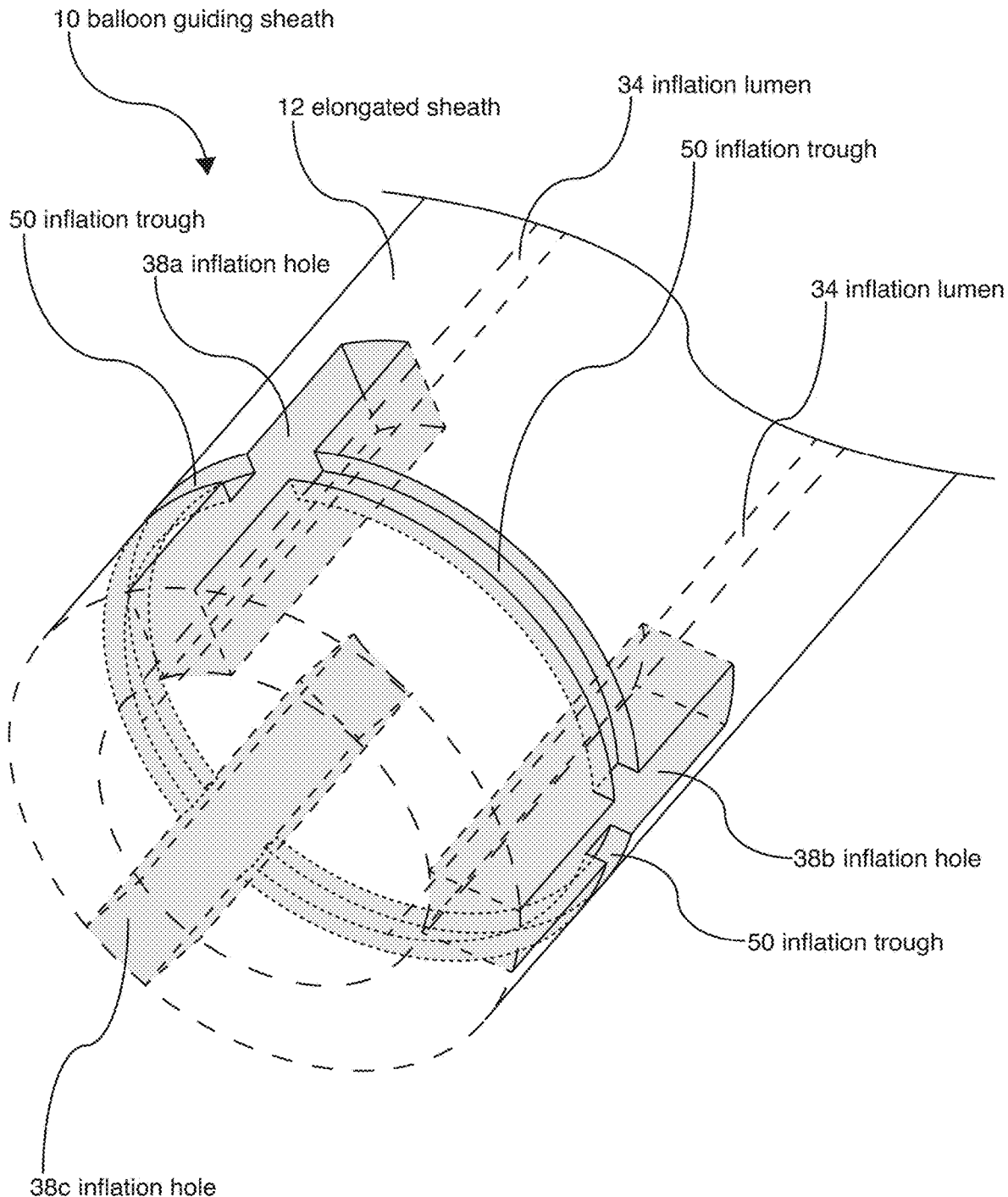

In many embodiments, each inflation hole 38 of the plurality of inflation holes are configured to fluidly couple to one another via at least one of the inflation lumen 34 and an inflation trough 50. The plurality of inflation holes may also be configured to fluidly couple the inflation lumen 34 to the inflation trough 50. In some embodiments, the inflation trough 50 is located between the inflatable balloon 30 and the outer tube 20. FIG. 4D in particular highlights, via shading, the at least one inflation hole 38 and the inflation trough 50. The inflation trough 50 may be thought of as an "etched out" layer of the outer tube 20, such that outer tube 20 defines inflation trough 50 in some examples. The inflation trough 50 may also be located on the outer tube 20. Fluid coupling between each inflation hole (i.e. in the illustrated embodiment, inflation holes 38a, 38b, and 38c) of the plurality of inflation holes may allow at least one of fluid and media to flow around the inflation trough 50 in order to maintain substantially even and substantially constant pressure and/or inflation of the inflatable balloon 30.

In some embodiments, the inflation trough 50 rotationally extends around at least a portion of a perimeter 52 (labeled in FIGS. 5B, 6B, 7A, and 7B) of the outer tube 20 in order to fluidly couple at least two inflation holes 38 of the plurality of inflation holes. The inflation trough 50 may rotationally extend about 360-degrees around the perimeter 52 of the outer tube 20 in order to fluidly couple each inflation hole 38 of the plurality of inflation holes. In some embodiments, the elongated sheath 12 is elongate along a first direction and the inflation trough 50 rotationally extends along a second direction that is perpendicular to the first direction. As such, the inflation trough 50 may extend radially out from the outer tube 20 in a direction perpendicular to the elongate direction of the elongated sheath. In some embodiments, the inflation trough 50 defines a depth radially extending along the second direction that is perpendicular to the first direction. The depth may be about 0.002 inches. In some embodiments, the inflation trough 50 defines a depth of 0.002 inches radially extending from an outer edge of the elongated sheath 12 toward the working lumen 26. The inflation trough 50 may define a depth of about 0.001 inches.

Figure 4E:
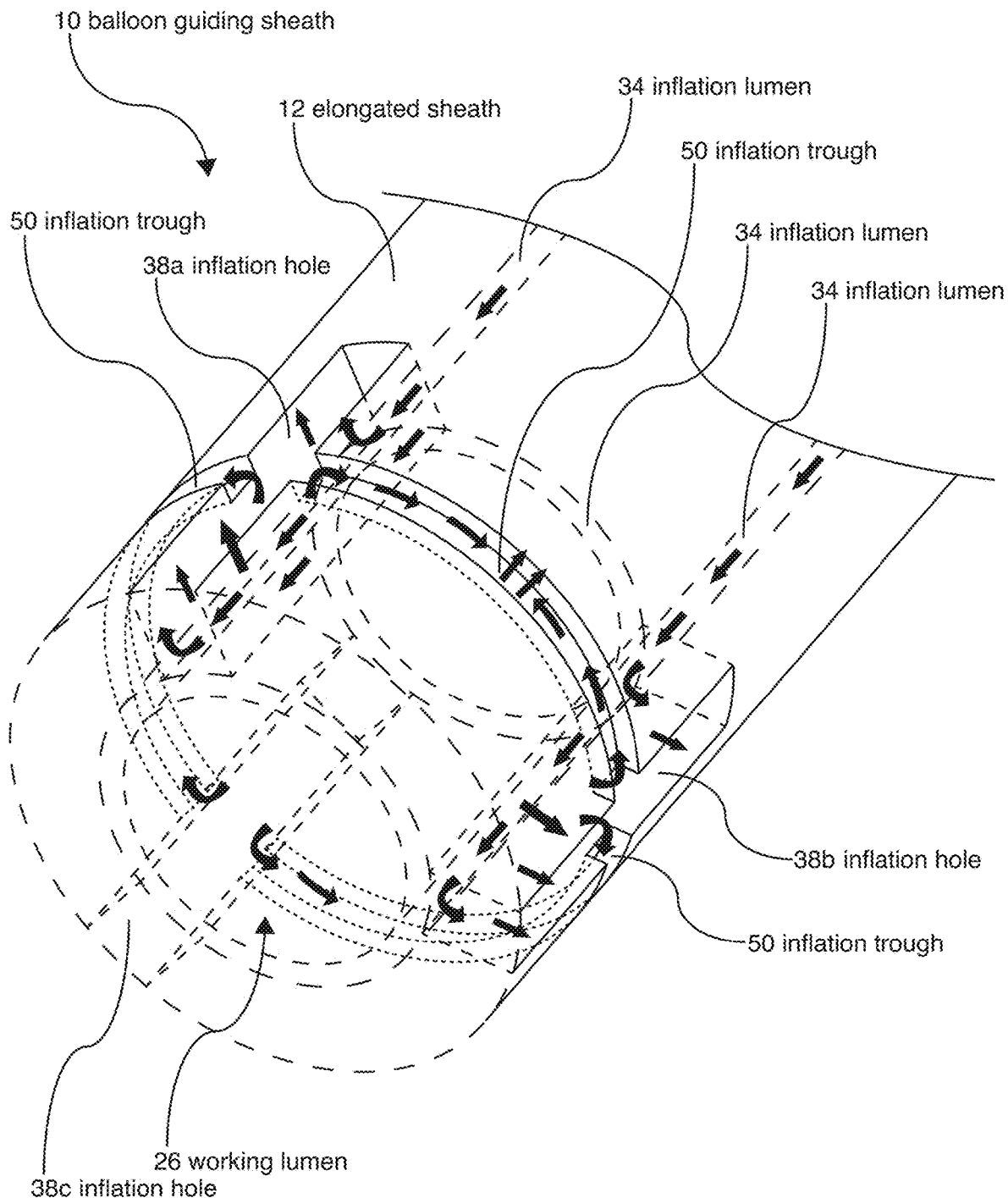

In some embodiments, the inflation holes 38 are elongate along the first direction, such that the elongated sheath 12 is elongate along the same direction as the inflation holes 38. Similar to the inflation trough 50, the at least one inflation hole 38 may define a depth radially extending from an outer edge of the elongated sheath 12 radially inward toward the working lumen 26. In some embodiments, the depth is 0.01 inches. The depth may be about 0.01 inches. In some embodiments, the depth of the inflation holes 38 is 0.005 inches. Referring now to FIG. 4E, in some embodiments, at least one of fluid and media is configured to flow from the inflation port 36, shown in FIGS. 1 and 3, through the inflation lumen 34, and to the at least one inflation hole 38 and inflation trough 50, in order to inflate the inflatable balloon 30 (not pictured). The arrows in FIG. 4E represent that the flow of fluid and/or media may proceed in a distal direction through the inflation lumen 34, radially outward through the at least one inflation hole 38, and then around the circumference of the elongated sheath 12 in the inflation trough 50. As previously discussed, substantially even inflation of the inflatable balloon 30 may be achieved by the substantially even distribution of fluid and/or media around the elongated sheath 12, which is enabled through the use of the at least one inflation hole 38 and inflation trough 50. The at least one inflation hole 38 and inflation trough 50 may be used to achieve full inflation, partial inflation, and/or deflation of the inflatable balloon 30. In some embodiments, partial inflation may be used to provide a layer of fluid and/or media between the inflatable balloon 30 and the outer surface of the elongated sheath 12 in an effort to reduce surface contact between the elongated sheath 12 and the inflatable balloon 30, without actually inflating the balloon 30 to the extent necessary to reduce blood flow during a thrombectomy procedure.

Figure 4F:
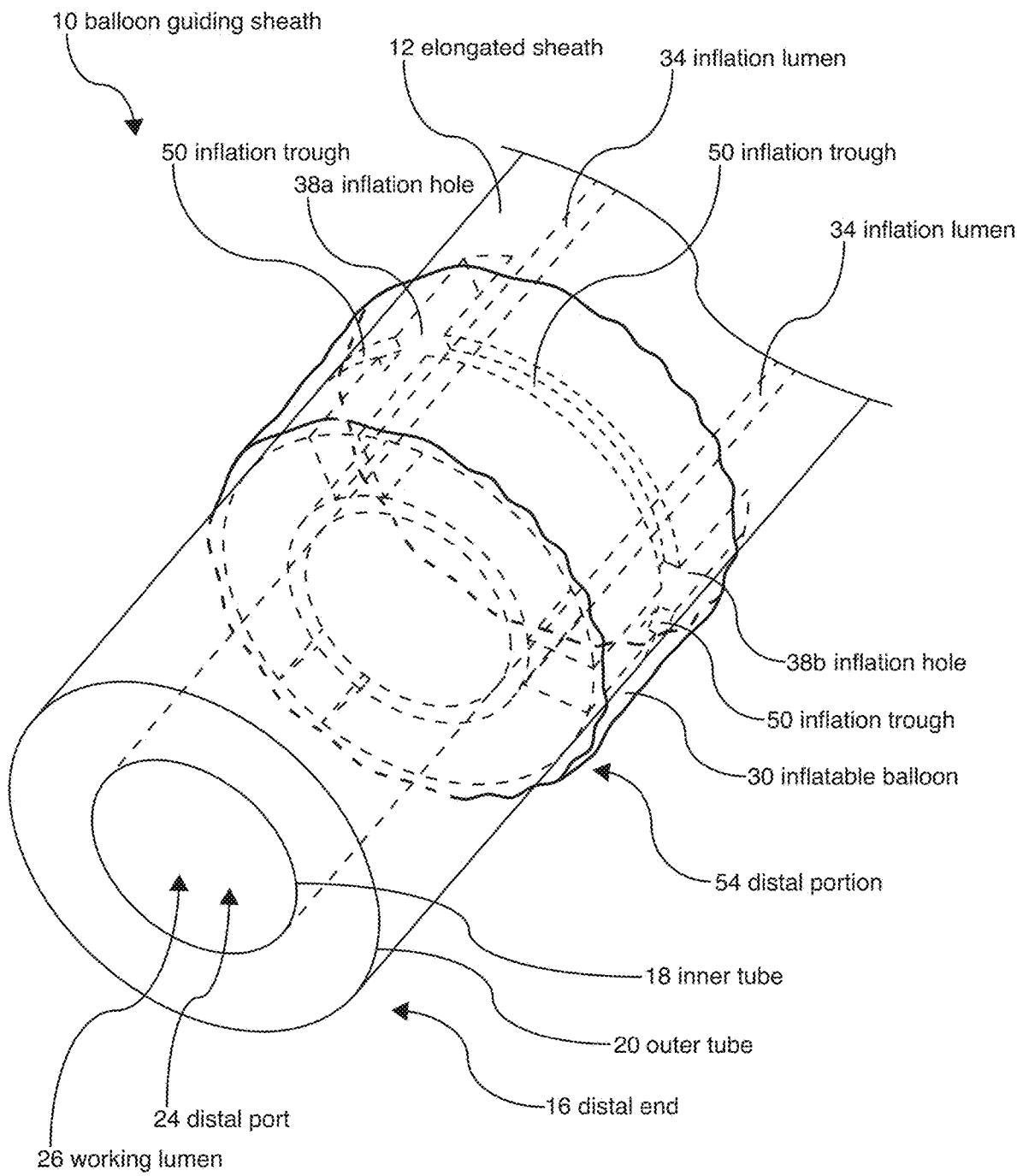
Figure 4G:
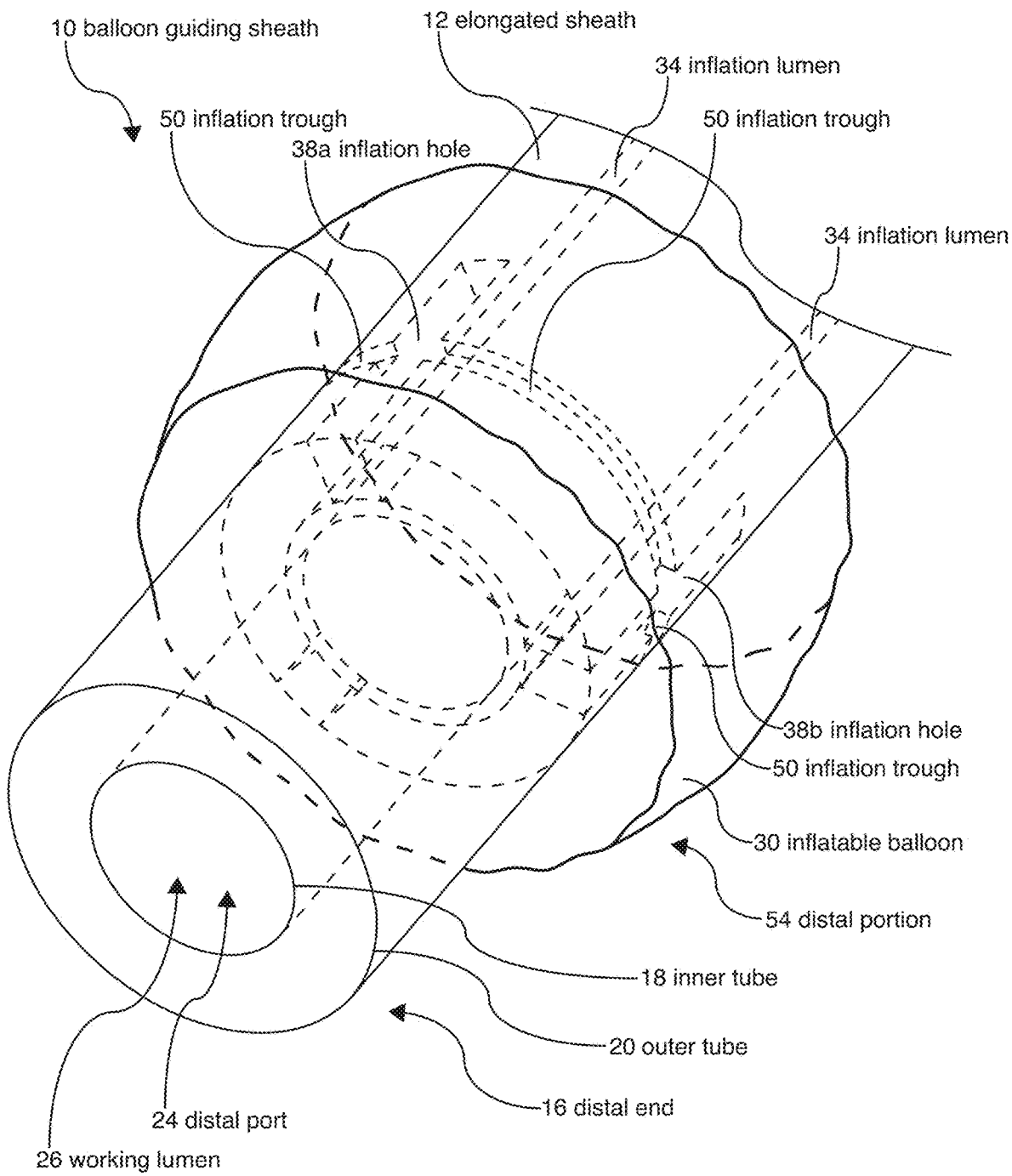

FIGS. 4F and 4G include the inflatable balloon 30, and show it at different stages of inflation. FIG. 4F shows the balloon 30 at least one of substantially deflated and only partially inflated, while FIG. 4G demonstrates full inflation, according to some embodiments. FIG. 4G shows that, in some embodiments, the inflatable balloon 30 achieves substantially even inflation, which, as previously discussed, may comprise radial symmetry of the inflated balloon 30. The inflatable balloon 30 may also inflate in an asymmetrical manner. FIGS. 4F and 4G also include the distal end 16 of the elongated sheath 12, and illustrate that, in some embodiments, the inflatable balloon 30 is located near the distal end 16. The inflatable balloon 30 may be located closer to the distal end 16 than is shown in FIGS. 4F and 4G. In some embodiments, the inflatable balloon 30 is located further from the distal end 16 than shown in the Figures. As also shown in FIG. 3, FIGS. 4F and 4G show that, in many embodiments, the inflatable balloon 30 is located substantially directly over the inflation trough 50 and the at least one inflation hole 38.

Figure 5A:
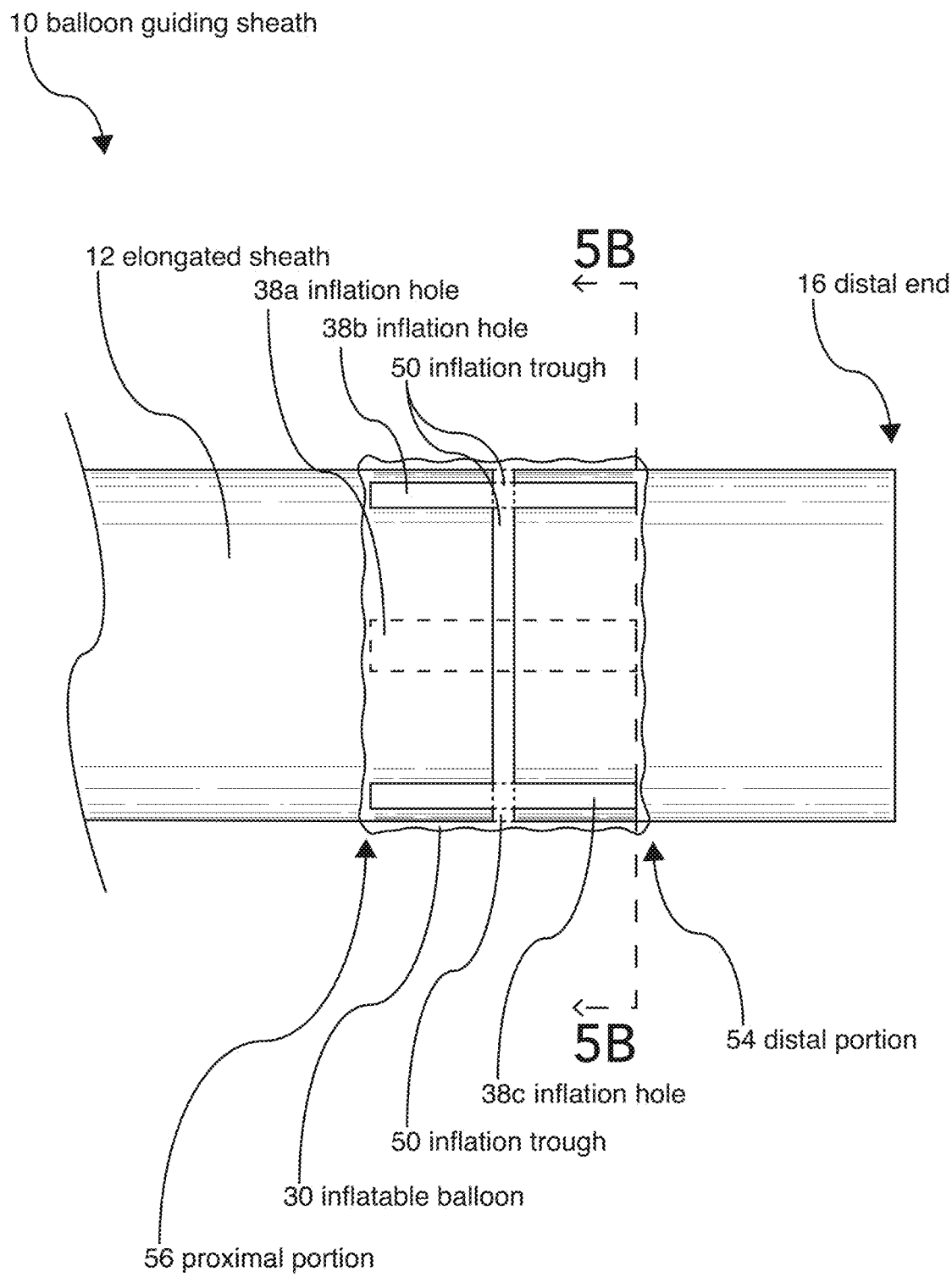
FIG. 5A illustrates a side view of a balloon guiding sheath, according to some embodiments.
Figure 6A:
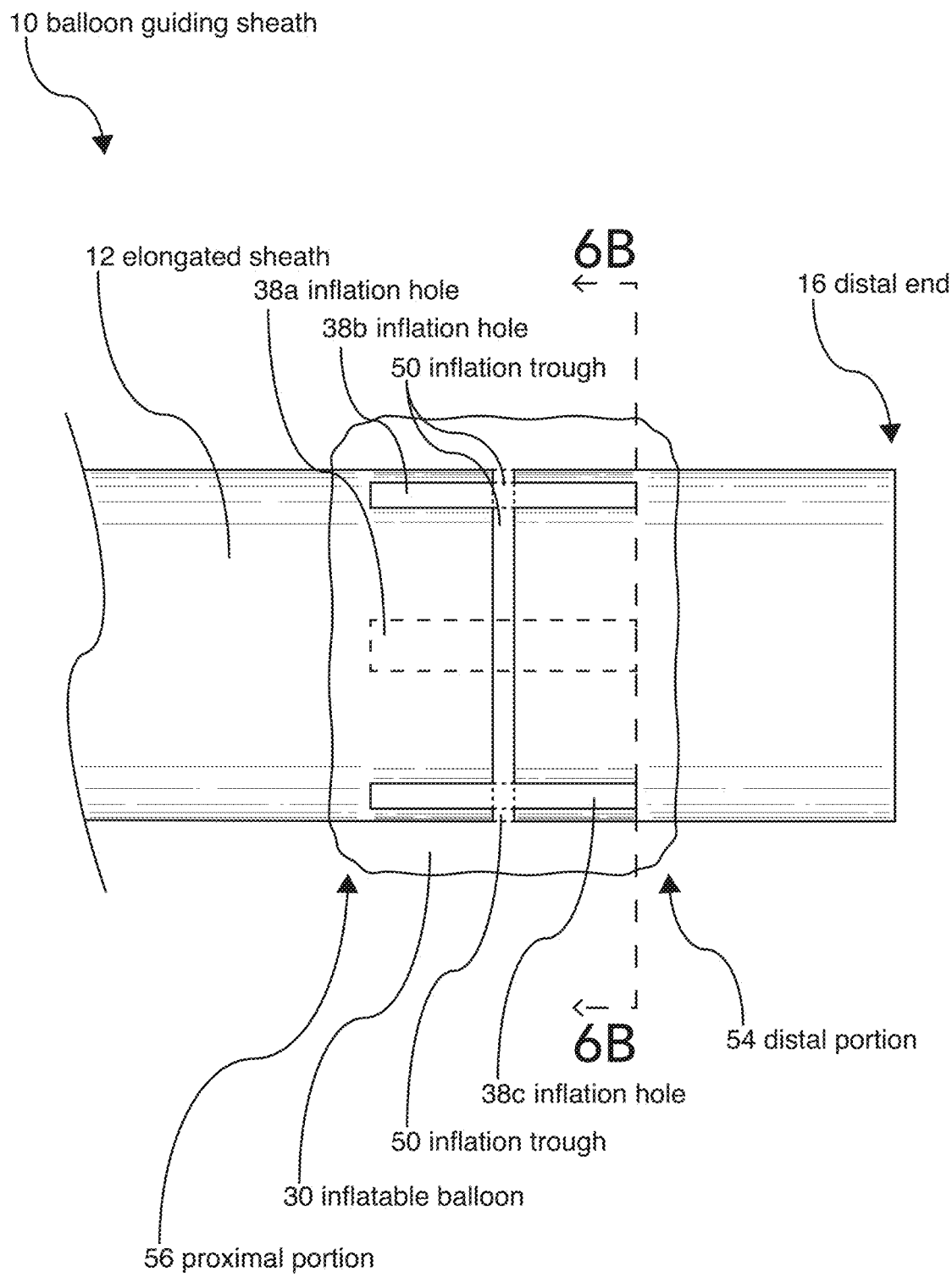
FIG. 6A illustrates a side view of a balloon guiding sheath, according to some embodiments.

FIGS. 5A and 6A each show a side view of the balloon guiding sheath 10, according to some embodiments. FIGS. 5A and 6A may each also represent a top and/or bottom view of the sheath 10. The figures include the elongated sheath 12, the at least one inflation hole 38, the inflation trough 50, the distal end 16 of the elongated sheath 12, the inflatable balloon 30, and the proximal 56 and distal 54 portions of the balloon 30. In some embodiments, the inflation trough 50 is located substantially evenly between the proximal portion 56 and the distal portion 54 of the inflatable balloon 30. The inflation trough 50 may be located closer to the proximal portion 56 than the distal portion 54. In some embodiments, the inflation trough 50 is located closer to the distal portion 54 than the proximal portion 56. The at least one inflation hole 38 may be substantially centered below the inflatable balloon 30, or may be located closer to the proximal portion 56 or the distal portion 54 of the balloon 30. FIG. 5A shows the inflatable balloon 30 in a deflated state, while FIG. 6A shows the balloon 30 in an inflated state. In some embodiments, the balloon 30 is configured to inflate to a greater extent than illustrated by FIG. 6A. The balloon 30 may be configured to inflate to a lesser extent than illustrated by FIG. 6A.

Figure 5B:
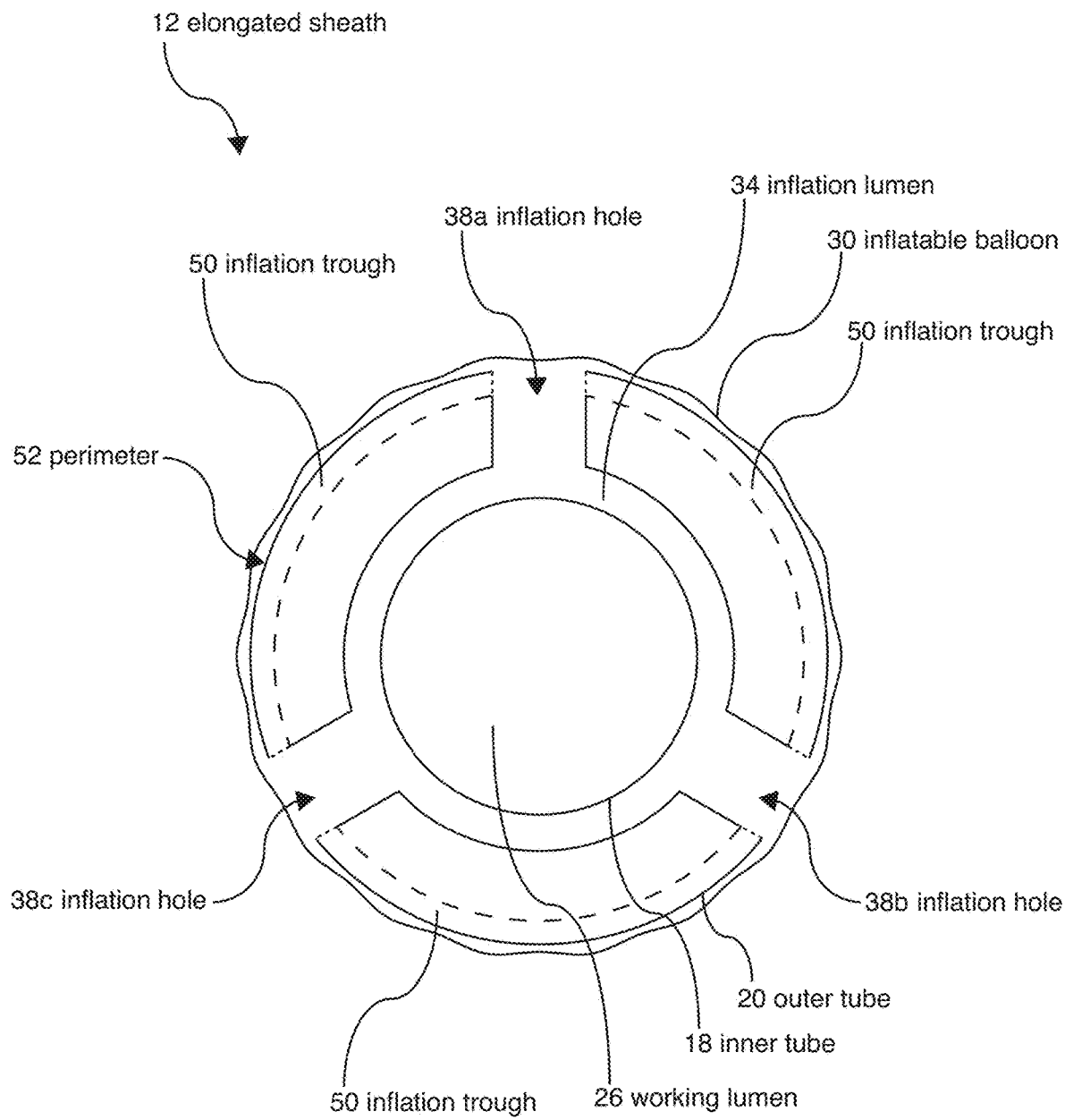
FIG. 5B illustrates a cross-sectional view of a portion of a balloon guiding sheath, according to some embodiments.
Figure 6B:
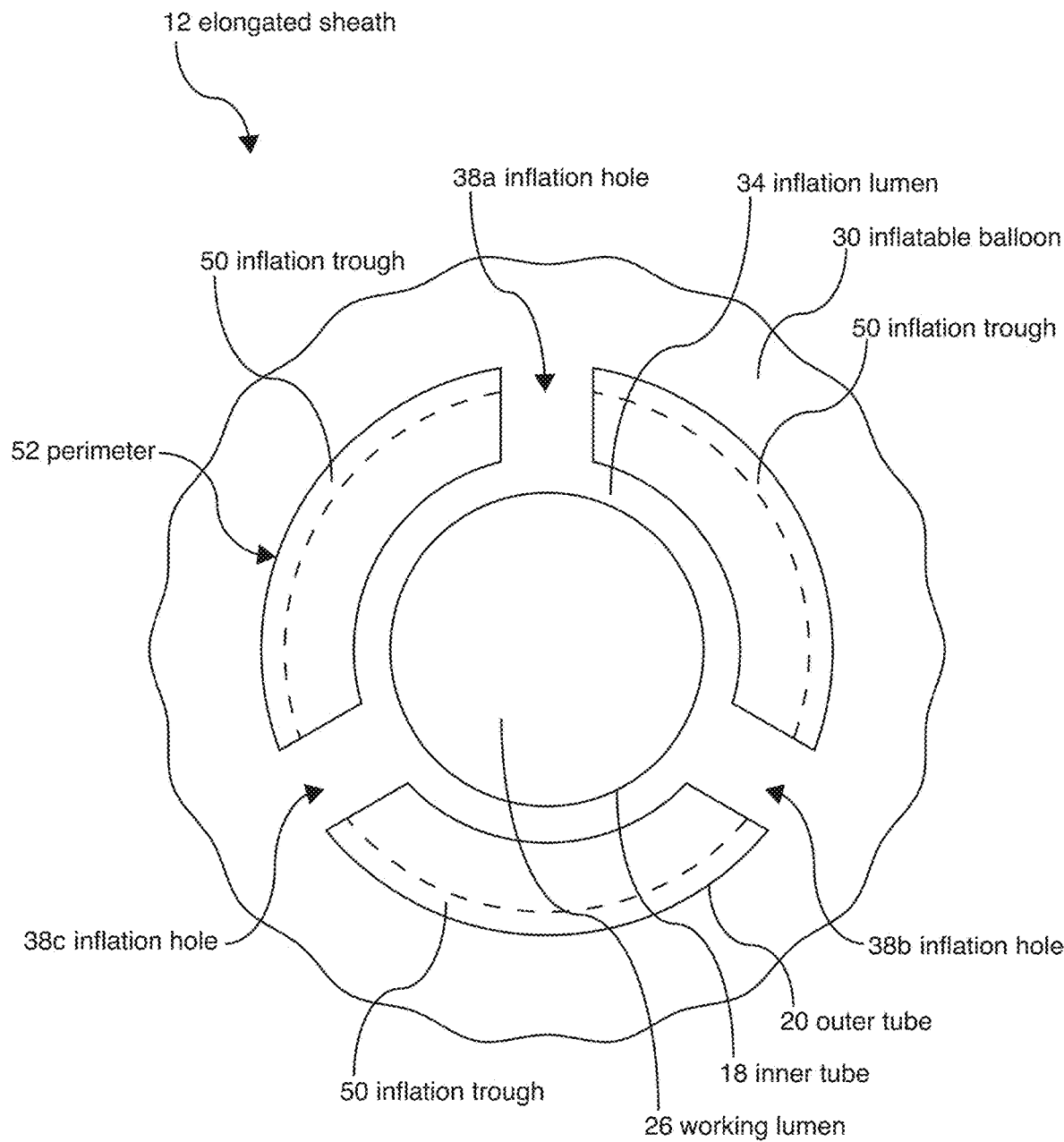
FIG. 6B illustrates a cross-sectional view of an elongated sheath, according to some embodiments.

FIGS. 5B and 6B each show a cross-sectional view of the portion of the elongated sheath 12 designated in FIGS. 5A and 6A, respectively. FIGS. 5B and 6B each include the working lumen 26, the inner tube 18, the outer tube 20, the at least one inflation hole 38, the inflation trough 50, the perimeter 52 of the outer tube 20, and the inflatable balloon 30. Similar to FIGS. 5A and 6A, FIG. 5B shows the balloon 30 in a deflated state and FIG. 6B shows the balloon 30 in an inflated state. As previously discussed, in many embodiments, the at least one inflation hole 38 is a plurality of inflation holes 38 comprise three inflation holes 38a, 38b, and 38c substantially evenly spaced around the perimeter 52 of the outer tube 20. FIGS. 5B and 6B also show the inflation trough 50 located near the perimeter 52 of the outer tube 20, as previously described. It should be noted that though the figures illustrate the inflatable balloon 30 in a generally circular shape, the balloon 30 may define any number of suitable shapes. In addition, FIG. 6B illustrates that, in many embodiments, the balloon 30 achieves substantially symmetrical inflation such that the balloon 30 comprises a consistent diameter. However, the balloon 30 may also inflate in an asymmetrical manner and comprise a varying diameter.

Figure 7A:
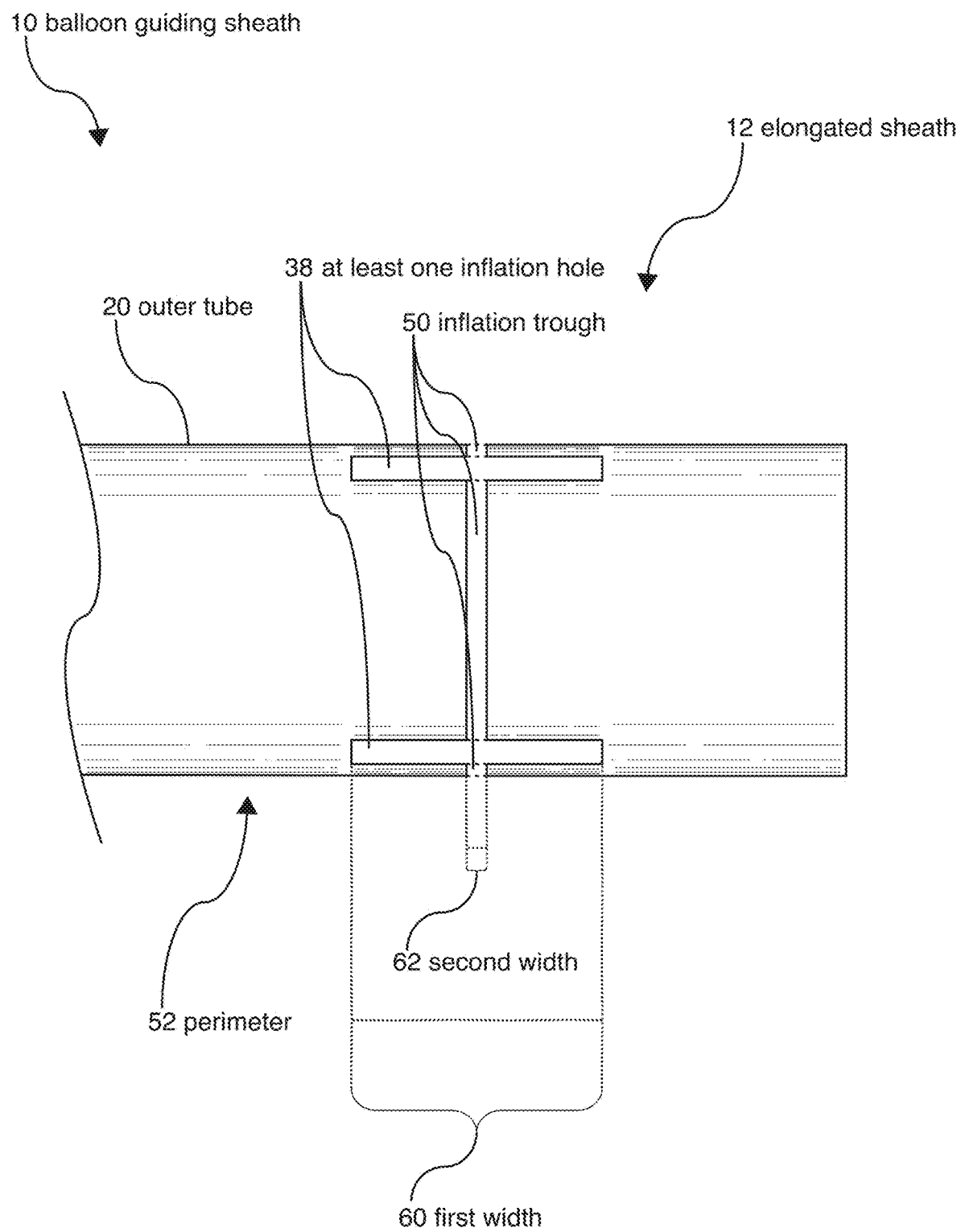
FIGS. 7A and 7B illustrate perspective views of a distal portion of a balloon guiding sheath, according to some embodiments.
Figure 7B:
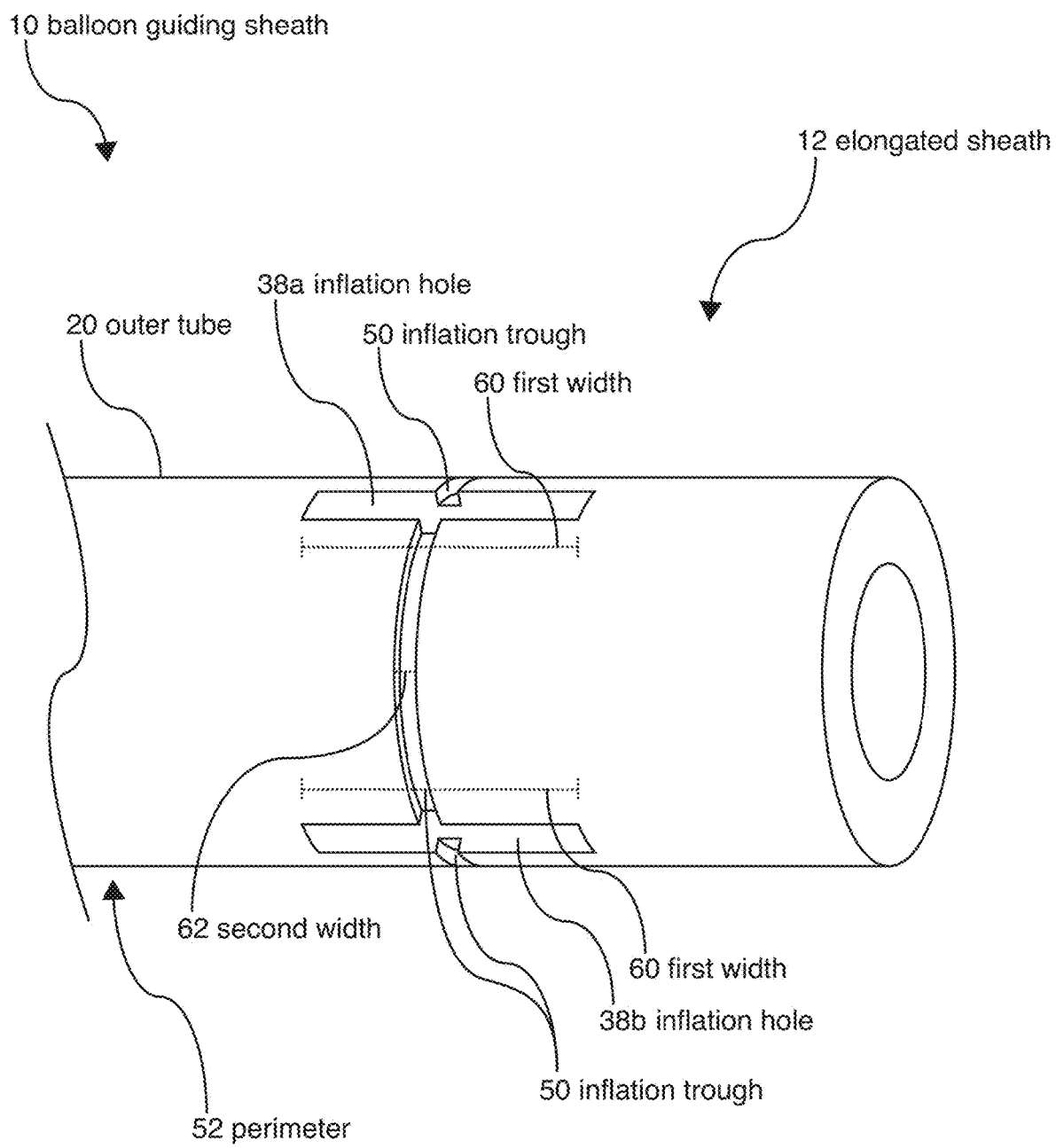

FIGS. 7A and 7B show 2D and 3D side views, respectively, of a distal portion of the balloon guiding sheath 10, according to some embodiments. As shown by the figures, in some embodiments, each inflation hole 38 defines a first width 60 and the inflation trough 50 defines a second width 62, and the first width 60 defines a larger width than the second width 62. In some embodiments, the second width 62 defines a larger width than the first width 60. The first width 60 and the second width 62 may be relatively close in dimension, or may vary in dimension, as demonstrated in FIGS. 7A and 7B. The elongated sheath 12 may be elongate along a first direction and both the first width 60 and the second width 62 extend along the first direction.

Figure 8A:
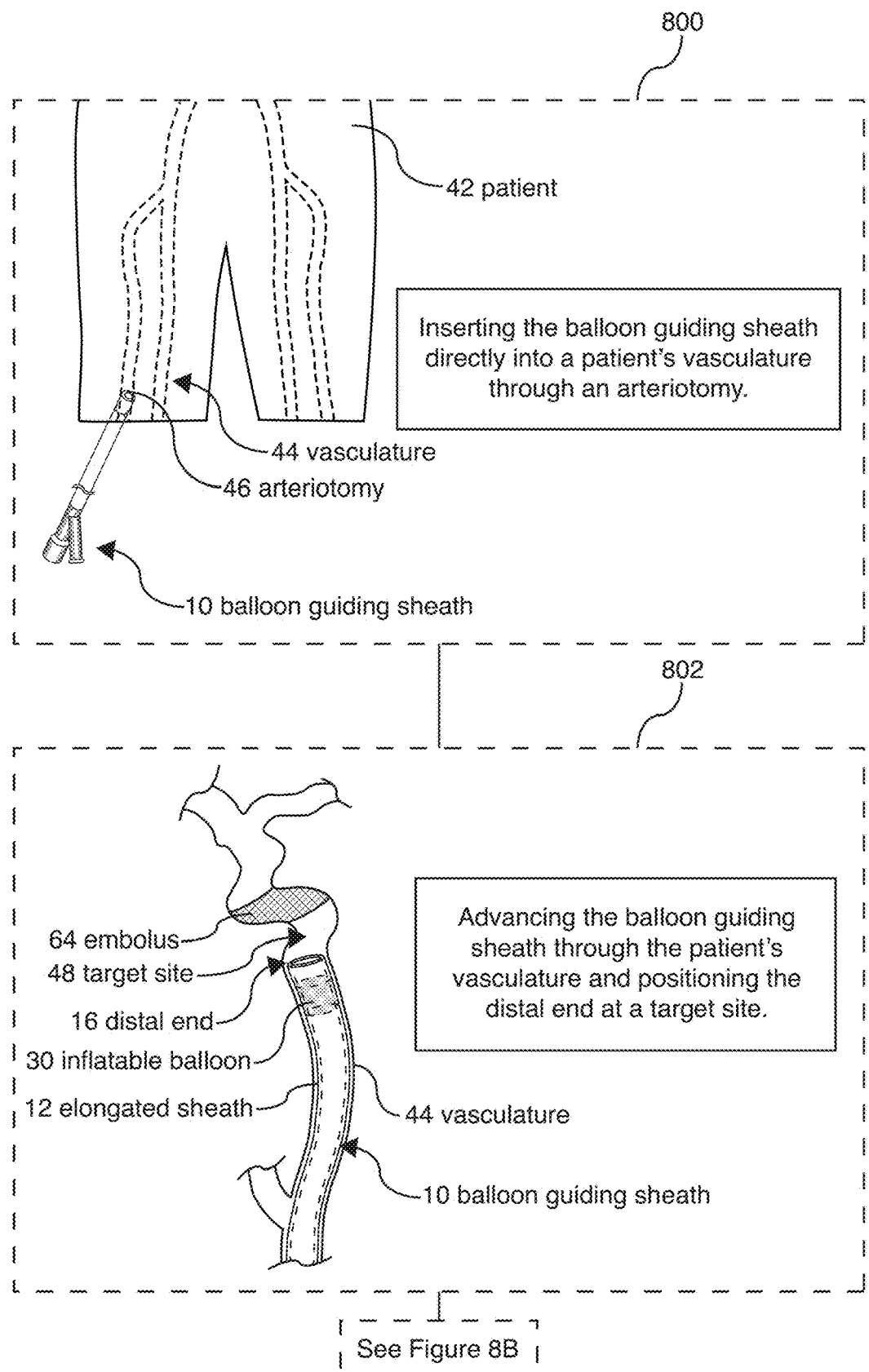
FIGS. 8A and 8B illustrate a method of using a balloon guiding sheath, according to some embodiments.
Figure 8B:
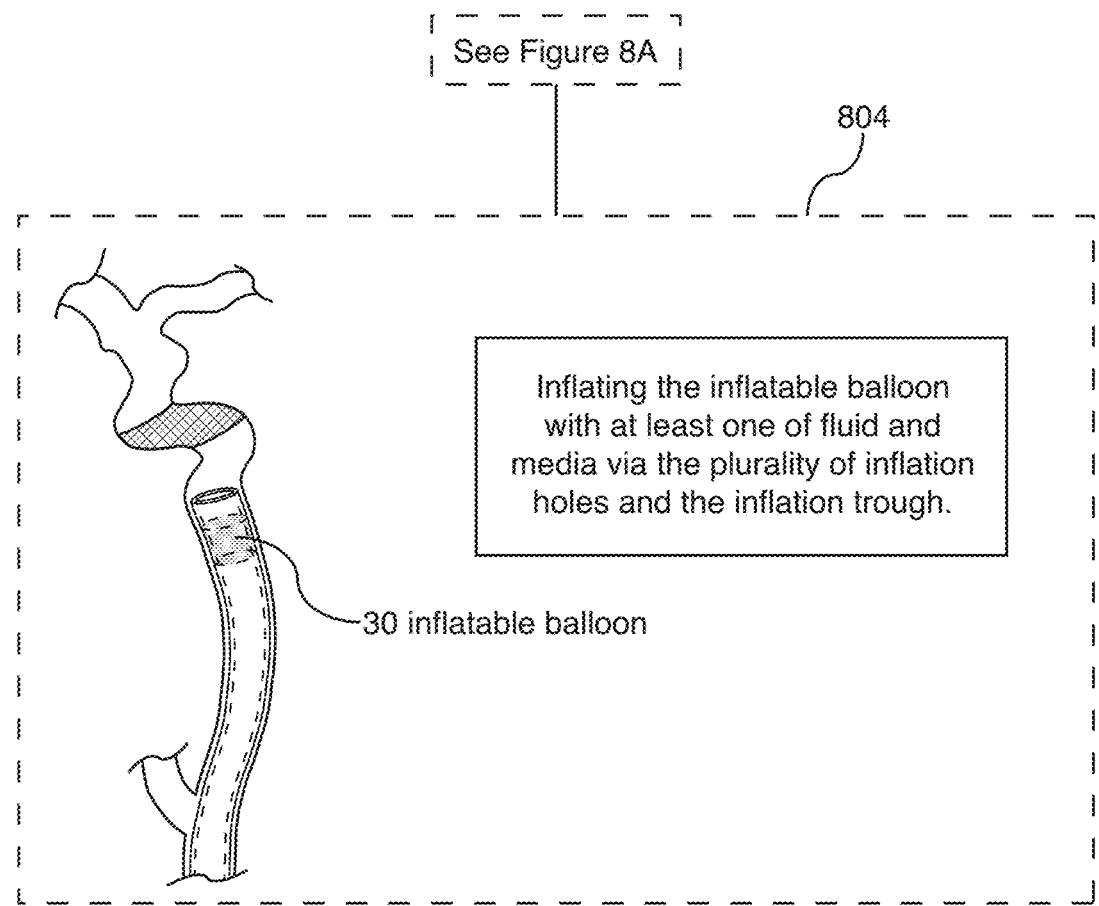

FIGS. 8A and 8B illustrate a method of using the balloon guiding sheath 10, according to some embodiments. As shown by step 800 of FIG. 8A, in some embodiments, the method comprises inserting the balloon guiding sheath 10 directly into a patient's 42 vasculature 44 through an arteriotomy 46. As previously mentioned, the arteriotomy 46 may be located in a variety of arteries of a patient 42, including but not limited to: a femoral artery, a vertebral artery, and a radial artery. FIG. 8A demonstrates the arteriotomy 46 located in the thigh of the patient 42 to enable femoral access into the vasculature 44. Step 802 shows that the method may further comprise advancing the balloon guiding sheath 10 through the patient's 42 vasculature 44 and positioning the distal end 16 at a target site 48. As discussed with reference to FIG. 2, in some embodiments the target site 48 is located adjacent an embolus 64 in the ICA 44b, such that when the balloon guiding sheath 10 is located at the target site 48, the sheath 10 is in position to remove the embolus 64.

FIG. 8B, at step 804, illustrates inflating the inflatable balloon 30 with at least one of fluid and media via the plurality of inflation holes and the inflation trough 50. In some embodiments, inflating the balloon 30 comprises substantially symmetrically inflating the balloon. The inflatable balloon 30 may also be inflated in an asymmetrical manner. In order to achieve substantially symmetrical inflation, the method may comprise applying a substantially even inflation force into the inflatable balloon 30 via the plurality of inflation holes and the inflation trough 50. In some embodiments, the inflation force radially extends around a perimeter 52 of the elongated sheath 12, and the inflation force is directed away from the elongated sheath 12 to thereby substantially symmetrically inflate the inflatable balloon 30 with radial symmetry. The method may also comprise maintaining a substantially constant and even pressure within the inflatable balloon 30 in order to maintain even inflation.

In some embodiments, during step 804 of inflating the inflatable balloon 30, the method comprises maintaining a location of the distal end 16 of the elongated sheath 12 such that the distal end 16 is substantially located in the first position adjacent the target site 48, as illustrated in step 802 of FIG. 8A. After the inflating, the method may comprise continuing to maintain the location of the distal end 16 of the elongated sheath 12 such that the distal end 16 is still substantially located in the first position after inflating the inflatable balloon 30.

As previously discussed, in many embodiments, the inflating (step 804) comprises injecting, via the inflation port 36, at least one of fluid and media into the inflation lumen 34, through the plurality of inflation holes and the inflation trough 50, and into the inflatable balloon 30. In some embodiments, the elongated sheath 12 is elongate along a first direction and the inflation trough 50 defines a depth radially extending along a second direction that is perpendicular to the first direction. The inflating may comprise sending (e.g., introducing) the at least one of fluid and media through the inflation lumen 34 along the first direction, sending the at least one of fluid and media through the plurality of inflation holes along the second direction, sending the at least one of fluid and media through the inflation trough 50 rotationally around the outer tube 20, and sending the at least one of fluid and media radially along the second direction away from the elongated sheath 12 to thereby inflate the inflatable balloon 30.

It should be noted that the components of the balloon guiding sheath 10 may be formed of any suitable material including, but not limited to, hard and/or soft polymer plastics, rubber, metallic materials, and any combination thereof. Any biocompatible material that may be structurally suitable may be used to form any component or components of the balloon guiding sheath 10. The fluid and/or media used to inflate the inflatable balloon 30 may comprise saline or a similar solution. In the event suction is used to remove an embolus 64, an external vacuum force may be applied to the distal end 16 of the elongated sheath 12, such as to the access port 22. The inflatable balloon 30 may comprise one layer or may comprise a plurality of layers. In some embodiments, the elongated sheath 12 has a degree of flexibility to allow a user (i.e. a medical professional) to maneuver the balloon guiding sheath 10 through the vasculature 44 of a patient 42.

INTERPRETATION

None of the steps described herein is essential or indispensable. Any of the steps can be adjusted or modified. Other or additional steps can be used. Any portion of any of the steps, processes, structures, and/or devices disclosed or illustrated in one embodiment, flowchart, or example in this specification can be combined or used with or instead of any other portion of any of the steps, processes, structures, and/or devices disclosed or illustrated in a different embodiment, flowchart, or example. The embodiments and examples provided herein are not intended to be discrete and separate from each other.

The section headings and subheadings provided herein are nonlimiting. The section headings and subheadings do not represent or limit the full scope of the embodiments described in the sections to which the headings and subheadings pertain. For example, a section titled "Topic 1" may include embodiments that do not pertain to Topic 1 and embodiments described in other sections may apply to and be combined with embodiments described within the "Topic 1" section.

To increase the clarity of various features in certain figures, some features are not labeled in each figure. Additionally, some figures may omit features to more clearly illustrate various features.

The various features and processes described above may be used independently of one another, or may be combined in various ways. All possible combinations and subcombinations are intended to fall within the scope of this disclosure. In addition, certain method, event, state, or process blocks may be omitted in some implementations. The methods, steps, and processes described herein are also not limited to any particular sequence, and the blocks, steps, or states relating thereto can be performed in other sequences that are appropriate. For example, described tasks or events may be performed in an order other than the order specifically disclosed. Multiple steps may be combined in a single block or state. The example tasks or events may be performed in serial, in parallel, or in some other manner. Tasks or events may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

The term "and/or" means that "and" applies to some embodiments and "or" applies to some embodiments. Thus, A, B, and/or C can be replaced with A, B, and C written in one sentence and A, B, or C written in another sentence. A, B, and/or C means that some embodiments can include A and B, some embodiments can include A and C, some embodiments can include B and C, some embodiments can only include A, some embodiments can include only B, some embodiments can include only C, and some embodiments can include A, B, and C. The term "and/or" is used to avoid unnecessary redundancy.

The term "about" may be used to mean "approximately". For example, the disclosure includes "The inflation trough 50 may rotationally extend about 360-degrees around the perimeter 52 of the outer tube 20 in order to fluidly couple each inflation hole 38 of the plurality of inflation holes." In this context, "about 360-degrees" is used to mean "approximately 360-degrees". Any value between 270 and 360-degrees may fall within the range of "about 360-degrees" as used in the disclosure.

The term "substantially" may be used to mean "nearly completely" or "for the most part." For example, the disclosure includes "the plurality of inflation holes are substantially symmetrically spaced around the outer tube." In this context, "substantially symmetrically" means that the inflation holes are completely or nearly completely symmetrically spaced around the outer tube.

While certain example embodiments have been described, these embodiments have been presented by way of example only, and are not intended to limit the scope of the inventions disclosed herein. Thus, nothing in the foregoing description is intended to imply that any particular feature, characteristic, step, module, or block is necessary or indispensable to implement the embodiments disclosed. Indeed, the novel methods and systems described herein may be embodied in a variety of other forms; furthermore, various omissions, substitutions, and changes in the form of the methods, devices, and systems described herein may be made without departing from the spirit of the inventions disclosed herein.

What is claimed is:

1. A balloon guiding sheath, comprising:
   an elongated sheath comprising a proximal end, a distal end, an inner tube extending between the proximal end and the distal end, an outer tube surrounding the inner tube and extending between the proximal end and the distal end, an access port located adjacent the proximal end, a distal port located adjacent the distal end, and a working lumen extending through an interior portion of the elongated sheath between the access port and the distal port;
   an inflatable balloon located on an outer surface of the elongated sheath adjacent the distal end, the inflatable balloon being fluidly coupled to an inflation lumen extending between the inflatable balloon and an inflation port located adjacent the proximal end; and
   a plurality of inflation holes extending through a side wall of the elongated sheath, wherein the plurality of inflation holes fluidly couple the inflatable balloon to the inflation lumen,
   wherein the elongated sheath is sized and configured to enable direct insertion into a patient's vasculature through an arteriotomy to position the inflatable balloon at a target site,
   wherein the outer tube defines an inflation trough configured to facilitate fluid coupling between the plurality of inflation holes, and
   wherein the elongated sheath is elongate along a first direction, at least one inflation hole of the plurality of inflation holes defines a first width extending along the first direction, and the inflation trough defines a second width extending along the first direction, and wherein the first width is greater than the second width.

2. The balloon guiding sheath of claim 1, wherein the inflation trough rotationally extends around at least a portion of a perimeter of the outer tube to fluidly couple at least two inflation holes of the plurality of inflation holes.

3. The balloon guiding sheath of claim 1, wherein the inflation trough rotationally extends 360-degrees around a perimeter of the outer tube to fluidly couple the plurality of inflation holes.

4. The balloon guiding sheath of claim 1, wherein the inflation trough rotationally extends along a second direction that is perpendicular to the first direction.

5. The balloon guiding sheath of claim 1, wherein the plurality of inflation holes are substantially symmetrically spaced around the outer tube.

6. The balloon guiding sheath of claim 1, wherein the plurality of inflation holes and the inflation trough are arranged and configured to facilitate substantial symmetrical inflation of the inflatable balloon.

7. The balloon guiding sheath of claim 1, wherein an outer surface of the outer tube defines the inflation trough.

8. The balloon guiding sheath of claim 1, wherein the inflation trough is located adjacent the distal end of the elongated sheath.

9. The balloon guiding sheath of claim 1, wherein the inflation trough is located closer to a distal portion of the inflatable balloon than a proximal portion of the inflatable balloon.

10. The balloon guiding sheath of claim 1, wherein the inflation trough defines a depth radially extending along a second direction that is perpendicular to the first direction.

11. The balloon guiding sheath of claim 1, wherein the elongated sheath defines a generally constant outer diameter from the proximal end to the distal end.

12. A method comprising:
   inserting a balloon guiding sheath directly into a patient's vasculature through an arteriotomy in at least one of a carotid artery or a vertebral artery, the balloon guiding sheath comprising:
   an elongated sheath comprising a proximal end, a distal end, an inner tube extending between the proximal end and the distal end, an outer tube surrounding the inner tube and extending between the proximal end and the distal end, an access port located adjacent the proximal end, a distal port located adjacent the distal end, and a working lumen extending through an interior portion of the elongated sheath between the access port and the distal port;
   an inflatable balloon located on an outer surface of the elongated sheath adjacent the distal end, the inflatable balloon being fluidly coupled to an inflation lumen extending between the inflatable balloon and an inflation port located adjacent the proximal end;

a plurality of inflation holes extending through a side wall of the elongated sheath, wherein the plurality of inflation holes fluidly couple the inflatable balloon to the inflation lumen; and an inflation trough defined by the outer tube, wherein the inflation trough facilitates fluid coupling between the plurality of inflation holes, and wherein the elongated sheath is elongate along a first direction, at least one inflation hole of the plurality of inflation holes defines a first width extending along the first direction, and the inflation trough defines a second width extending along the first direction, and wherein the first width is greater than the second width;

advancing the balloon guiding sheath through the patient's vasculature and positioning the distal end at a target site; and inflating the inflatable balloon with at least one of fluid or media via the plurality of inflation holes and the inflation trough.

13. The method of claim 12, wherein inflating the inflatable balloon comprises substantially symmetrically inflating the inflatable balloon via the plurality of inflation holes and the inflation trough.

14. The method of claim 12, wherein inflating the inflatable balloon comprises applying a substantially even inflation force into the inflatable balloon, via the plurality of inflation holes and the inflation trough, whereby the inflation force radially extends around a perimeter of the elongated sheath and the inflation force is directed away from the elongated sheath to thereby substantially symmetrically inflate the inflatable balloon.

15. The method of claim 14, further comprising maintaining a substantially constant and even pressure within the inflatable balloon.

16. The method of claim 12, wherein prior to the inflating the distal end of the elongated sheath is located in a first position with respect to the target site, the method further comprising, while inflating, maintaining a location of the distal end of the elongated sheath such that the distal end is substantially located in the first position during the inflating.

17. The method of claim 16, further comprising, after the inflating, maintaining the location of the distal end of the elongated sheath such that the distal end is still substantially located in the first position after the inflating.

18. The method of claim 12, wherein the inflation trough defines a depth radially extending along a second direction that is perpendicular to the first direction, the method further comprising:

sending the at least one of fluid or media through the inflation lumen along the first direction;

sending the at least one of fluid or media through the plurality of inflation holes along the second direction;

sending the at least one of fluid or media through the inflation trough rotationally around the outer tube; and sending the at least one of fluid or media radially along the second direction away from the elongated sheath to thereby inflate the inflatable balloon.

19. A balloon guiding sheath, comprising:

an elongated sheath comprising a proximal end, a distal end, an inner tube extending between the proximal end and the distal end, an outer tube surrounding the inner tube and extending between the proximal end and the distal end, an access port located adjacent the proximal end, a distal port located adjacent the distal end, and a working lumen extending through an interior portion of the elongated sheath between the access port and the distal port;

an inflatable balloon located on an outer surface of the elongated sheath adjacent the distal end, the inflatable balloon being fluidly coupled to an inflation lumen extending between the inflatable balloon and an inflation port located adjacent the proximal end; and a plurality of inflation holes extending through a side wall of the elongated sheath, wherein the plurality of inflation holes fluidly couple the inflatable balloon to the inflation lumen, wherein the elongated sheath is sized and configured to enable direct insertion into a patient's vasculature through an arteriotomy to position the inflatable balloon at a target site, and wherein the outer tube defines an inflation trough configured to facilitate fluid coupling between the plurality of inflation holes, and wherein the inflation trough is located closer to a distal portion of the inflatable balloon than a proximal portion of the inflatable balloon.

20. The balloon guiding sheath of claim 19, wherein the plurality of inflation holes and the inflation trough are arranged and configured to facilitate substantial symmetrical inflation of the inflatable balloon.

* * * * *